(12) United States Patent
Davies et al.

(10) Patent No.: US 7,619,065 B2
(45) Date of Patent: Nov. 17, 2009

(54) CYSTINE-KNOT FOLD PROTEIN

(75) Inventors: Mark Douglas Davies, London (GB); Christopher Benjamin Phelps, London (GB); Richard Joseph Fagan, London (GB); Christine Power, Thoiry (FR); Melanie Yorke, Confignon (CH); Mark Ibberson, Gimel (CH)

(73) Assignee: Ares Trading S.A., Aubonne (CH)

( * ) Notice: Subject to any disclaimer, the term of this patent is extended or adjusted under 35 U.S.C. 154(b) by 114 days.

(21) Appl. No.: 10/872,898

(22) Filed: Jun. 21, 2004

(65) Prior Publication Data

US 2005/0186663 A1   Aug. 25, 2005

Related U.S. Application Data

(63) Continuation-in-part of application No. PCT/GB02/05865, filed on Dec. 20, 2002.

(30) Foreign Application Priority Data

Dec. 21, 2001  (GB) ................................. 0130738.8

(51) Int. Cl.
*C07H 21/04* (2006.01)
*C12P 21/02* (2006.01)
*C07K 14/52* (2006.01)

(52) U.S. Cl. .................... 530/351; 435/69.5; 435/320.1

(58) Field of Classification Search ........................ None
See application file for complete search history.

(56) References Cited

U.S. PATENT DOCUMENTS 7,193,069 B2 * 3/2007 Isogai et al. ............... 536/23.1

FOREIGN PATENT DOCUMENTS

WO   WO 03/055911   7/2003

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Whisstock et al., Prediction of protein function from protein sequence and structure. Quaterly Reviews of Biophysics, 36, 307-340, 2003.*
Wistow et al., tau-enolase/alpha enolase:One gene encodes bothe an enzyme and a lens structural protein. J. Cell. Biol., 107, 2729-2736, 1988).*
Foley et al., Embryonic heart induction, Ann.N.Y.Acad.Sci., 1080, 85-96, 2006.*
de Caestecker, M, Transforming growth factor-b receptor superfamily, Encyclopedia of Biol. Chem., 4, 2004-abstract.*
Avsian-Kretchmer et al. Comparative Genomic Analysis of the Eight-Membered RingCystine Knot-Containing Bone Morphogenetic Protein Antagonists, Mol. Endocrinol., 18, 1-12, 2004.*
XP—002066227, Tewis Bouwmeester, et al., "Cerberus is a head-inducing secreted factor expressed in the anterior endoderm of Spemann's organizer", Nature, vol. 382, Aug. 15, 1996, pp. 595-601.
XP—002245163, Peter M. Eimon, et al., "Xenopus Dan, a member of the Dan gene family of BMP antagonists, is expressed in derivatives of the cranial and trunk neural crest", Mechanisms of Development, vol. 107, (2001), pp. 187-189.
XP—002245164, *Homo sapiens* (human).
XP—002245164, *Homo sapiens* (human), Feb. 28, 2002.
Jonathan J. H. Pearce, et al., A Mouse Cerberus/Dan-Related Gene Family, Development Biology (1999) vol. 209, p. 98-110 .
Binwu Tang, et al. TGF-β Switches From Tumor Suppressor to Prometastatic Factor in A Model of Breast Cancer Progression, The Journal ofClinical Investigation (2003) vol. 112, No. 7, p. 1116-1124.
Yoshihiro Morinaga, et al., Stimulation Of Interleukin-11 Production From Osteoblast-Like Cells by Transforming Growth Factor-β And Tumor Cell Factors, Int. J. Cancer (1997) vol. 71, p. 422-428.

* cited by examiner

*Primary Examiner*—Lorraine Spector
*Assistant Examiner*—Elly-Gerald Stoica
(74) *Attorney, Agent, or Firm*—Frommer Lawrence & Haug LLP; Thomas J. Kowalski; Ljiljana Minwalla

(57) ABSTRACT

This invention relates to a novel protein (INSP002), herein identified as a secreted protein that is a member of the Dan family of the cystine-knot fold cytokine superfamily and to the use of this protein and nucleic acid sequences from the encoding genes in the diagnosis, prevention and treatment of disease.

3 Claims, 24 Drawing Sheets

Figure 1: Top ten NCBI non-redundant database BLAST hits against INSP002

```
Query= INSP002
        (189 letters)

Database: ncbi-nt
        1,021,646 sequences; 4,527,726,597 total letters

Searching..............................................done
```

|  | Score<br>(bits) | E<br>Value |
|---|---|---|
| Sequences producing significant alignments: | | |
| gi\|15217064\|gb\|AF400435.1\|AF400435 Homo sapiens cerberus-related... | 69 | 2e-10 |
| gi\|11427432\|ref\|XM_005320.1\| Homo sapiens cerberus 1 (Xenopus la... | 69 | 2e-10 |
| gi\|4885134\|ref\|NM_005454.1\| Homo sapiens cerberus 1 (Xenopus lae... | 69 | 2e-10 |
| gi\|5802091\|gb\|AF139721.1\|AF139721 Gallus gallus cerberus homolog... | 68 | 3e-10 |
| gi\|5902633\|gb\|AF179484.1\|AF179484 Gallus gallus caronte (CAR) mR... | 67 | 5e-10 |
| gi\|2853615\|gb\|AF035579.1\|AF035579 Mus musculus cerberus homolog ... | 61 | 5e-08 |
| gi\|6753409\|ref\|NM_009887.1\| Mus musculus cerberus 1 homolog (Xen... | 61 | 5e-08 |
| gi\|2654026\|gb\|AF031896.1\|AF031896 Mus musculus cerberus-related ... | 61 | 5e-08 |
| gi\|1513087\|gb\|U64831.1\|XLU64831 Xenopus laevis head-inducing fac... | 57 | 9e-07 |
| gi\|6679017\|ref\|NM_008675.1\| Mus musculus neuroblastoma, suppress... | 55 | 3e-06 |

Figure 2: Alignment with top hit, Homo sapiens cerberus-related 1

```
>gi|15217064|gb|AF400435.1|AF400435 Homo sapiens cerberus-related 1
       (CER1) mRNA, complete cds
      Length = 804

Score = 68.9 bits (167), Expect = 2e-10
 Identities = 36/102 (35%), Positives = 53/102 (51%)
 Frame = +1

Query: 87   VTLPLNPQEVIQGMCKAVPFVQVFSRPGCSAIRLRNHLCFGHCSSLYIPGSDPTPLVLCN 146
            V LP+    EV   C+ VPF Q  + GC  + ++N+LCFG C S++ PG+      C+
Sbjct: 442  VILPIKSHEVHWETCRTVPFSQTITHEGCEKVVVQNNLCFGKCGSVHFPGAAQHSHTSCS 621

Query: 147  SCMPARKRWAPVVLWCLTGSSASRRRVKISTMLIEGCHCSPK 188
            C+PA+    + L C   SS    +K+ ML+E C C K
Sbjct: 622  HCLPAKFTTMHLPLNCTELSSV----IKV-VMLVEECQCKVK 732
```

Figure 3: Top four NCBI-nr and NCBI-nt database BLAST hits against INSP002 i) ncbi-nr

```
Database: All non-redundant GenBank CDS
translations+PDB+SwissProt+PIR+PRF
           1,242,768 sequences; 395,571,179 total letters Searching..................................................done Score      E
Sequences producing significant alignments:             (bits)   Value ref|NP_689867.1| hypothetical protein FLJ38607 [Homo sapiens] >g...  394   e-109
ref|XP_113990.1| hypothetical protein XP_113990 [Homo sapiens]      221   5e-57
ref|XP_164658.1| similar to hypothetical protein FLJ38607 [Homo ...  70   1e-11
ref|NP_005445.1| cerberus 1; cerberus-related 1; cerberus 1 (Xen...  69   3e-11
gb|AAD51610.1|AF139721_1 cerberus homolog [Gallus gallus]            68   6e-11
``` ii) ncbi-nt

```
Database: All GenBank+EMBL+DDBJ+PDB sequences (but no EST, STS, GSS,
or phase 0, 1 or 2 HTGS sequences)
           1,469,831 sequences; 7,238,625,236 total letters Searching..................................................done Score      E
Sequences producing significant alignments:             (bits)   Value ref|NM_152654.1| Homo sapiens hypothetical protein FLJ38607 (FLJ...  394   e-108
dbj|AK095926.1| Homo sapiens cDNA FLJ38607 fis, clone HEART2004941   394   e-108
gb|BC025333.1| Homo sapiens, clone IMAGE:4558384, mRNA, partial cds  221   e-103
ref|XM_113990.1| Homo sapiens LOC199699 (LOC199699), mRNA           221   e-103
gb|AC092069.2| Homo sapiens chromosome 19 clone CTC-425F1, compl... 222   1e-56
```

Figure 4: Alignment of INSP002 with AK095926.1

```
>dbj|AK095926.1| Homo sapiens cDNA FLJ38607 fis, clone HEART2004941
          Length = 1731

Score =  394 bits (1013), Expect = e-108
 Identities = 189/189 (100%), Positives = 189/189 (100%)
 Frame = +2

Query: 1     MLLGQLSTLLCLLSGALPTGSGRPEPQSPRPQSWAAANQTWALGPGALPPLVPASALGSW 60
             MLLGQLSTLLCLLSGALPTGSGRPEPQSPRPQSWAAANQTWALGPGALPPLVPASALGSW
Sbjct: 44    MLLGQLSTLLCLLSGALPTGSGRPEPQSPRPQSWAAANQTWALGPGALPPLVPASALGSW 223

Query: 61    KAFLGLQKARQLGMGRLQRGQDEVAAVTLPLNPQEVIQGMCKAVPFVQVFSRPGCSAIRL 120
             KAFLGLQKARQLGMGRLQRGQDEVAAVTLPLNPQEVIQGMCKAVPFVQVFSRPGCSAIRL
Sbjct: 224   KAFLGLQKARQLGMGRLQRGQDEVAAVTLPLNPQEVIQGMCKAVPFVQVFSRPGCSAIRL 403

Query: 121   RNHLCFGHCSSLYIPGSDPTPLVLCNSCMPARKRWAPVVLWCLTGSSASRRRVKISTMLI 180
             RNHLCFGHCSSLYIPGSDPTPLVLCNSCMPARKRWAPVVLWCLTGSSASRRRVKISTMLI
Sbjct: 404   RNHLCFGHCSSLYIPGSDPTPLVLCNSCMPARKRWAPVVLWCLTGSSASRRRVKISTMLI 583

Query: 181   EGCHCSPKA 189
             EGCHCSPKA
Sbjct: 584   EGCHCSPKA 610
```

Figure 5: Alignment of INSP002 with IMAGE: 4558384

```
>gb|BC025333.1| Homo sapiens, clone IMAGE:4558384, mRNA, partial cds
          Length = 1746

Score =  221 bits (562), Expect(2) = e-103
 Identities = 108/108 (100%), Positives = 108/108 (100%)
 Frame = +1

Query: 1     MLLGQLSTLLCLLSGALPTGSGRPEPQSPRPQSWAAANQTWALGPGALPPLVPASALGSW 60
             MLLGQLSTLLCLLSGALPTGSGRPEPQSPRPQSWAAANQTWALGPGALPPLVPASALGSW
Sbjct: 187   MLLGQLSTLLCLLSGALPTGSGRPEPQSPRPQSWAAANQTWALGPGALPPLVPASALGSW 366

Query: 61    KAFLGLQKARQLGMGRLQRGQDEVAAVTLPLNPQEVIQGMCKAVPFVQ 108
             KAFLGLQKARQLGMGRLQRGQDEVAAVTLPLNPQEVIQGMCKAVPFVQ
Sbjct: 367   KAFLGLQKARQLGMGRLQRGQDEVAAVTLPLNPQEVIQGMCKAVPFVQ 510

Score =  178 bits (451), Expect(2) = e-103
 Identities = 81/81 (100%), Positives = 81/81 (100%)
 Frame = +2

Query: 109   VFSRPGCSAIRLRNHLCFGHCSSLYIPGSDPTPLVLCNSCMPARKRWAPVVLWCLTGSSA 168
             VFSRPGCSAIRLRNHLCFGHCSSLYIPGSDPTPLVLCNSCMPARKRWAPVVLWCLTGSSA
Sbjct: 596   VFSRPGCSAIRLRNHLCFGHCSSLYIPGSDPTPLVLCNSCMPARKRWAPVVLWCLTGSSA 775

Query: 169   SRRRVKISTMLIEGCHCSPKA 189
             SRRRVKISTMLIEGCHCSPKA
Sbjct: 776   SRRRVKISTMLIEGCHCSPKA 838
```

Figure 6: INSP002 nucleotide sequence with translation

```
  1  AAATGCCTCC CAGGCTATCC AGGAGGGGCC AAGAGATTAA AAGCAGGTTC AGAAGGCTCA
 61  GATGCCACTC ACCAGACAGC AGGGTCGACT GCTAGTGACC TTGAGCCCAG TCCGGACAGA
121  CAGACAGGCA GACAGACGCA CGGACAAGCA GATGCTCCTT GGCCAGCTAT CCACTCTTCT
                                           m  l  l    g  q  l    s  t  l

181  GTGCCTGCTT AGCGGGGCCC TGCCTACAGG CTCAGGGAGG CCTGAACCCC AGTCTCCTCG
      l  c  l  l    s  g  a    l  p  t    g  s  r    p  e  p    q  s  p

241  ACCTCAGTCC TGGGCTGCAG CCAATCAGAC CTGGGCTCTG GGCCAGGGG  CCCTGCCCCC
      r  p  q  s    w  a  a    n  q    t  w  a  l    g  p  g    a  l  p

301  ACTGGTGCCA GCTTCTGCCC TTGGGAGCTG AAGGCCTTC  TTGGGCCTGC AGAAAGCCAG
      p  l  v  p    a  s    l  g  s    w  k  a  f    l  g  l    q  k  a

361  GCAGCTGGGG ATGGGCAGGC TGCAGCGTGG GCAAGACGAG GTGGCTGCTG TGACTCTGCC
      r  q  l  g    m  g  r    l  q  r    g  q  d  e    v  a  a    v  t  l

421  GCTGAACCCT CAGGAAGTGA TCCAGGGGAT GTGTAAGGCT GTGCCCTTCG TTCAGGTGTT
      p  l  n  p    q  e  v    i  q  g    m  c  k  a    v  p  f    v  q  v

481  CTCCCGGCCC GGCTGCTCAG CCATACGCCT CCGAAATCAT CTGTGCTTTG GTCATTGCTC
      f  s  r  p    g  c   s  a  i   r   l  r  n  h    l  c  f    g  h  c
                           INSP002-CP1

541  CTCTCTCTAC ATCCCTGGCT CGGACCCCAC CCCACTAGTC CTGTGCAACA GCTGTATGCC
      s  s  l  y    i  p  g    s  d  p    t  p  l  v    l  c  n    s  c  m

601  TGCTCGCAAG CGTTGGGCAC CCGTGGTCCT GTGGTGTCTC ACTGGCAGCT CAGCCTCCCG
      p  a  r  k    r  w  a    p  v  v    l  w  c  l   t  g  s    s  a  s
                                                        INSP002-CP2

661  TCGACGGGTG AAGATATCCA CCATGCTGAT CGAGGGGTGT CACTGCAGCC CAAAAGCATG
      r  r  r  v    k  i  s    t  m  l    i  e  g  c    h  c  s    p  k  a

721  AACTGAGCAT CGTGGATGGG TGCACGGAGA CACGCACCTT GGAGAAATGA GGGGAGAT
```

Figure 7: INSP002 partial cloned sequence with translation

```
  1   CTCAGCCATA CGCCTCCGAA ATCATCTGTG CTTTGGTCAT TGCTCCTCTC TCTACATCCC
        s   a   i    r   l   r    n   h   l    c   f   g    h   c   s    s   l   y   i

61   TGGCTCGGAC CCCACCCCAC TAGTCCTGTG CAACAGCTGT ATGCCTGCTC GCAAGCGTTG
        p   g   s    d   p   t    p   l   v    l   c   n    s   c   m    p   a   r   k   r

121   GGCACCCGTG GTCCTGTGGT GTCTCACTGG CAGCTCAGC
        w   a   p    v   v   l    w   c   l    t   g   s    s
```

Figure 8: Map of PCRII-TOPO-INSP002 partial

```
Molecule:        product1,  4109 bps DNA Circular
File Name:       ~7879480.cm5

Description:     Ligation of NoName into PCRII-TOPO-open

Molecule Features:

Type        Start        End      Name         Description

REGION          1        336                   LacZa'
MARKER        239                 SP6
GENE          337        495      INSP002 partial cds Inserted PCR product
REGION        496        747                   'LacZa
MARKER        584               C T7
REGION        749       1163                   f1 ori
GENE         1497       2291      KanR         Kanamycin resistance gene
GENE         2309       3169      AmpR         Ampicillin resistance gene
GENE         3314       3987                   pUC ori
```

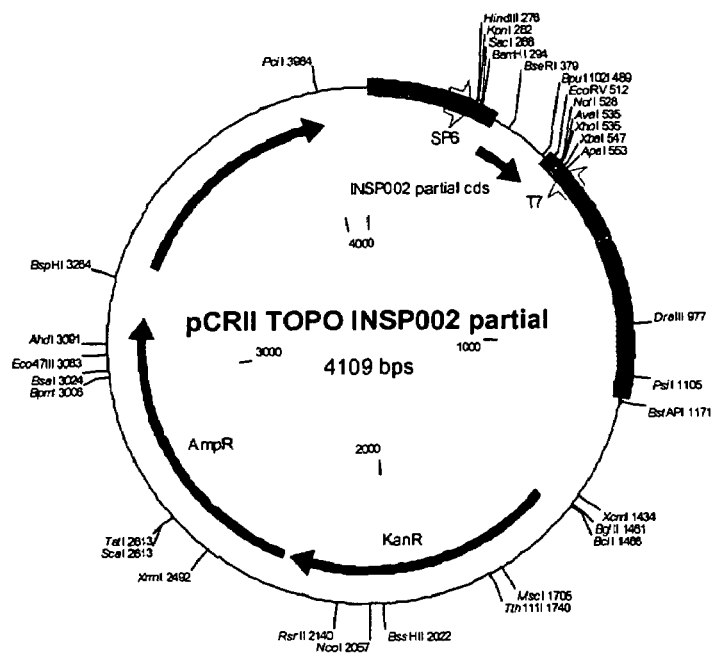

Figure 9: Alignment of INSP002 prediction (top) and partial cloned sequence (bottom)

Figure 9a: Alignment of nucleotide sequences

```
                10        20        30        40        50        60
INSPpr  CAGAAATGCCTCCCAGGCTATCCAGGAGGGGCCAAGAGATTAAAAGCAGGTTCAGAAGGC
        :
Serono  C-----------------------------------------------------------

70        80        90       100       110       120
INSPpr  TCAGATGCCACTCACCAGACAGCAGGGTCGACTGCTAGTGACCTTGAGCCCAGTCCGGAC

Serono  ------------------------------------------------------------

130       140       150       160       170       180
INSPpr  AGACAGACAGGCAGACAGACGCACGGACAAGCAGATGCTCCTTGGCCAGCTATCCACTCT

Serono  ------------------------------------------------------------

190       200       210       220       230       240
INSPpr  TCTGTGCCTGCTTAGCGGGGCCCTGCCTACAGGCTCAGGGAGGCCTGAACCCCAGTCTCC

Serono  ------------------------------------------------------------

250       260       270       280       290       300
INSPpr  TCGACCTCAGTCCTGGGCTGCAGCCAATCAGACCTGGGCTCTGGGCCCAGGGGCCCTGCC

Serono  ------------------------------------------------------------

310       320       330       340       350       360
INSPpr  CCCACTGGTGCCAGCTTCTGCCCTTGGGAGCTGGAAGGCCTTCTTGGGCCTGCAGAAAGC

Serono  ------------------------------------------------------------

370       380       390       400       410       420
INSPpr  CAGGCAGCTGGGGATGGGCAGGCTGCAGCGTGGGCAAGACGAGGTGGCTGCTGTGACTCT

Serono  ------------------------------------------------------------

430       440       450       460       470       480
INSPpr  GCCGCTGAACCCTCAGGAAGTGATCCAGGGGATGTGTAAGGCTGTGCCCTTCGTTCAGGT

Serono  ------------------------------------------------------------

490       500       510       520       530       540
INSPpr  GTTCTCCCGGCCCGGCTGCTCAGCCATACGCCTCCGAAATCATCTGTGCTTTGGTCATTG
                           ::::::::::::::::::::::::::::::::::
Serono  ------------------TCAGCCATACGCCTCCGAAATCATCTGTGCTTTGGTCATTG
                            10        20        30        40

550       560       570       580       590       600
INSPpr  CTCCTCTCTCTACATCCCTGGCTCGGACCCCACCCCACTAGTCCTGTGCAACAGCTGTAT
        ::::::::::::::::::::::::::::::::::::::::::::::::::::::::::::
Serono  CTCCTCTCTCTACATCCCTGGCTCGGACCCCACCCCACTAGTCCTGTGCAACAGCTGTAT
         50        60        70        80        90       100

610       620       630       640       650       660
INSPpr  GCCTGCTCGCAAGCGTTGGGCACCCGTGGTCCTGTGGTGTCTCACTGGCAGCTCAGCCTC
        :::::::::::::::::::::::::::::::::::::::::::::::::::::::::
Serono  GCCTGCTCGCAAGCGTTGGGCACCCGTGGTCCTGTGGTGTCTCACTGGCAGCTCAGC---
               110       120       130       140       150
```

Figure 9a continued

```
           670        680        690        700        710        720
INSPpr CCGTCGACGGGTGAAGATATCCACCATGCTGATCGAGGGGTGTCACTGCAGCCCAAAAGC

Serono ------------------------------------------------------------
```

Figure 9b: Alignment of protein sequences:

```
Serono ------------------------------------------------------------

INSP00 MLLGQLSTLLCLLSGALPTGSGRPEPQSPRPQSWAAANQTWALGPGALPPLVPASALGSW
            10        20        30        40        50        60

Serono                                                         SAIRL
                                                                :::::
INSP00 KAFLGLQXARQLGMGRLQRGQDEVAAVTLPLNPQEVIQGMCKAVPFVQVFSRPGCSAIRL
           70        80        90       100       110       120

10        20        30        40        50
Serono RNHLCFGHCSSLYIPGSDPTPLVLCNSCMPARKRWAPVVLWCLTGSSA-----------
       :::::::::::::::::::::::::::::::::::::::::::::::
INSP00 RNHLCFGHCSSLYIPGSDPTPLVLCNSCMPARKRWAPVVLWCLTGSSASRRRVKISTMLI
          130       140       150       160       170       180

Serono ---------

INSP00 EGCHCSPKA
```

Figure 10: Nucleotide sequence and translation of cDNA insert in Image:4558384

```
   1  CGGCACGAGG GGGAGACCTG GAAGGAAGCG ACTGCACTGA TCCAGAAATG CCTCCCAGGC
                      INSP002V-5'-F
  61  TATCCAGGAG GGGCCAAGAG ATTAAAAGCA GGTTCAGAAG GCTCAGATGC CACTCACCAG
 121  ACAGCAGGGT CGACTGCTAG TGACCTTGAG CCCAGTCCGG ACAGACAGAC AGGCAGACAG
                      INSP002V-5'nest-F
 181  ACGCACGGAC AAGCAGATGC TCCTTGGCCA GCTATCCACT CTTCTGTGCC TGCTTAGCGG
                                    m   l  l  g  q  l  s  t   l  l  c   l  l  s
 241  GGCCCTGCCT ACAGGCTCAG GGAGGCCTGA ACCCCAGTCT CCTCGACCTC AGTCCTGGGC
       g  a  l  p   t  g  s   g  r  p   e  p  q  s   p  r  p   q  s  w
 301  TGCAGCCAAT CAGACCTGGG CTCTGGGCCC AGGGGCCCTG CCCCCACTGG TGCCAGCTTC
       a  a  n   q  t  w   a  l  g   p  g  a  l   p  p  l   v  p  a
 361  TGCCCTTGGG AGCTGGAAGG CCTTCTTGGG CCTGCAGAAA GCCAGGCAGC TGGGGATGGG
       s  a  l  g   s  w  k   a  f  l   g  l  q  k   a  r  q   l  g  m
 421  CAGGCTGCAG CGTGGGCAAG ACGAGGTGGC TGCTGTGACT CTGCCGCTGA ACCCTCAGGA
       g  r  l  q   r  g  q   d  e  v   a  a  v  t   l  p  l   n  p  q
 481  AGTGATCCAG GGGATGTGTA AGGCTGTGCC CTTCGTTCAG ACACGGGAGT CTGGCTATGT
       e  v  i  q   g  m  c   k  a  v   p  f  v  q   t  r  e   s  r  y
                                              INSP002V-5'-R
 541  TGCCCAAGCT AGTCTTGAGC TTCTGGCCTC AAGCAATCCT CCCACCTCAG CCTCCTGAGT
       v  a  q  a   s  l  e   l  l  a   s  s  n  p   p  t  s   a  s
 601  TCTAGGTGTT CTCCCGGCCC GGCTGCTCAG CCATACGCCT CCGAAATCAT CTGTGCTTTG
                      INSP002V-3'-F
 661  GTCATTGCTC CTCTCTCTAC ATCCCTGGCT CGGACCCCAC CCCACTAGTC CTGTGCAACA
 721  GCTGTATGCC TGCTCGCAAG CGTTGGGCAC CCGTGGTCCT GTGGTGTCTC ACTGGCAGCT
 781  CAGCCTCCCG TCGACGGGTG AAGATATCCA CCATGCTGAT CGAGGGGTGT CACTGCAGCC
 841  CAAAAGCATG AACTGAGCAT CTGGATGGGT GCACGGAGAC ACGCACCTTG GAGAAATGAG
 901  GGGAGATGGA CCAAGAAAGA CGTGGACCTG GATGATGTAC TCTGGGTCAA GAGACCAGGG
                      INSP002V-3'nest-R
 961  ATGCAGGGTT AGGCAGACAG GTCCCCAGAG TCCTCACCCT GCTCCCCAGA CAGTAGACAC
1021  AGTGCCCGTC CTGGAGTTGC ACCACTGATA GTCACAGCAC ACAATGATTG ACAACTCACT
         INSP002V-3'-R
1081  TTTTTTTTT TTTTGAGAT GGAGTCTCGC TCTGTCGCCC AGGCTGGAGT GCAGTGGCGC
1141  AATCTCAGCT CACTGCAAGC TCCACCTCCC GGGTTATGC CATTCTCCTG TCTCAGCCTC
1201  CCGAGTAGCT GGGACTACAG GCACCCGCCA ACACGCCGG STAATTTTTT GTATTTTTAG
1261  TAAAGACAGG GTTTCACCGT GTTAGCCAGG ATGGTCTCTA TCTCCTGACC TCGTGATCTG
1321  CCTGCCTTGG CCTTATTATT TTTTTTTTAA GGACAGAGTC TCTCTCTGTC ACCCAGGCTG
1381  GAGTGCAATG GCGCGATCTT GGCTCACTGT AACTTCCACT TGCCAGGCTC AAGCAGTTCT
```

Figure 10 continued

```
1441  CCTGCCTCAG CCTCCTGAGT AGCTGGGACT ACAGGCACCC GCCACCATGC CCAGCTAATT
1501  TTTGTATTTT TAGTAGAGAC AGAGTTTCAC CATATTAGCC TGGCTGGTCT CAAACTCCTG
1561  GCCTCAGGTG ATCTGCCCAC CTCGGCCTCC CAAAGTGCTG GGATCAAATC CACTGTTAAT
1621  CATTAGGCTG AACTGTCTCT TATAGAATGA GGTCAAAGAC ACTCCCAGTT GCAGGGAGGG
1681  TAGATGGCCC CACCCAGACC GAGAGACACA GTGATGACCT CAGCCTAGGG ACMCCAAAAA
1741  AAAAAAAAAA AAAAAA
```

The position of the 87 bp insertion compared to the INSP002 prediction is highlighted.

The Alu sequence in the 3' non coding sequence is *italicised.*

Figure 11: Alignment of sequences of INSP002 prediction (top) with IMAGE: 4558384 (BC025333.1) (bottom)

Figure 11a: Nucleotide sequences

```
INSP00 ------------------------------CAGAAATGCCTCCCAGGCTATCCAGGAG
                                     ::::::::::::::::::::::::::::
BC0253 GGGAGACCTGGAAGGAAGCGACTGCACTGATCCAGAAATGCCTCCCAGGCTATCCAGGAG
                10        20        30        40        50        60

30        40        50        60        70        80
INSP00 GGGCCAAGAGATTAAAAGCAGGTTCAGAAGGCTCAGATGCCACTCACCAGACAGCAGGGT
       ::::::::::::::::::::::::::::::::::::::::::::::::::::::::::::
BC0253 GGGCCAAGAGATTAAAAGCAGGTTCAGAAGGCTCAGATGCCACTCACCAGACAGCAGGGT
                70        80        90       100       110       120

90       100       110       120       130       140
INSP00 CGACTGCTAGTGACCTTGAGCCCAGTCCGGACAGACAGACAGGCAGACAGACGCACGGAC
       ::::::::::::::::::::::::::::::::::::::::::::::::::::::::::::
BC0253 CGACTGCTAGTGACCTTGAGCCCAGTCCGGACAGACAGACAGGCAGACAGACGCACGGAC
               130       140       150       160       170       180

150       160       170       180       190       200
INSP00 AAGCAGATGCTCCTTGGCCAGCTATCCACTCTTCTGTGCCTGCTTAGCGGGGCCCTGCCT
       ::::::::::::::::::::::::::::::::::::::::::::::::::::::::::::
BC0253 AAGCAGATGCTCCTTGGCCAGCTATCCACTCTTCTGTGCCTGCTTAGCGGGGCCCTGCCT
              190       200       210       220       230       240

210       220       230       240       250       260
INSP00 ACAGGCTCAGGGAGGCCTGAACCCCAGTCTCCTCGACCTCAGTCCTGGGCTGCAGCCAAT
       ::::::::::::::::::::::::::::::::::::::::::::::::::::::::::::
BC0253 ACAGGCTCAGGGAGGCCTGAACCCCAGTCTCCTCGACCTCAGTCCTGGGCTGCAGCCAAT
              250       260       270       280       290       300

270       280       290       300       310       320
INSP00 CAGACCTGGGCTCTGGGCCCAGGGGCCCTGCCCCCACTGGTGCCAGCTTCTGCCCTTGGG
       ::::::::::::::::::::::::::::::::::::::::::::::::::::::::::::
BC0253 CAGACCTGGGCTCTGGGCCCAGGGGCCCTGCCCCCACTGGTGCCAGCTTCTGCCCTTGGG
              310       320       330       340       350       360

330       340       350       360       370       380
INSP00 AGCTGGAAGGCCTTCTTGGGCCTGCAGAAAGCCAGGCAGCTGGGGATGGGCAGGCTGCAG
       ::::::::::::::::::::::::::::::::::::::::::::::::::::::::::::
BC0253 AGCTGGAAGGCCTTCTTGGGCCTGCAGAAAGCCAGGCAGCTGGGGATGGGCAGGCTGCAG
              370       380       390       400       410       420

390       400       410       420       430       440
INSP00 CGTGGGCAAGACGAGGTGGCTGCTGTGACTCTGCCGCTGAACCCTCAGGAAGTGATCCAG
       ::::::::::::::::::::::::::::::::::::::::::::::::::::::::::::
BC0253 CGTGGGCAAGACGAGGTGGCTGCTGTGACTCTGCCGCTGAACCCTCAGGAAGTGATCCAG
              430       440       450       460       470       480

450       460       470
INSP00 GGGATGTGTAAGGCTGTGCCCTTCGTTCAG-------------------------------
       :::::::::::::::::::::::::::::::
BC0253 GGGATGTGTAAGGCTGTGCCCTTCGTTCAGACACGGGAGTCTCGCTATGTTGCCCAAGCT
              490       500       510       520       530       540

480
INSP00 ---------------------------------------------------------GTGTT
                                                                :::::
BC0253 AGTCTTGAGCTTCTGGCCTCAAGCAATCCTCCCACCTCAGCCTCCTGAGTTCTAGGTGTT
              550       560       570       580       590       600

490       500       510       520       530       540
INSP00 CTCCCGGCCCGGCTGCTCAGCCATACGCCTCCGAAATCATCTGTGCTTTGGTCATTGCTC
       ::::::::::::::::::::::::::::::::::::::::::::::::::::::::::::
BC0253 CTCCCGGCCCGGCTGCTCAGCCATACGCCTCCGAAATCATCTGTGCTTTGGTCATTGCTC
              610       620       630       640       650       660
```

Figure 11a continued

```
              550       560       570       580       590       600
INSP00  CTCTCTCTACATCCCTGGCTCGGACCCCACCCCACTAGTCCTGTGCAACAGCTGTATGCC
        ::::::::::::::::::::::::::::::::::::::::::::::::::::::::::::
BC0253  CTCTCTCTACATCCCTGGCTCGGACCCCACCCCACTAGTCCTGTGCAACAGCTGTATGCC
              670       680       690       700       710       720

610       620       630       640       650       660
INSP00  TGCTCGCAAGCGTTGGGCACCCGTGGTCCTGTGGTGTCTCACTGGCAGCTCAGCCTCCCG
        ::::::::::::::::::::::::::::::::::::::::::::::::::::::::::::
BC0253  TGCTCGCAAGCGTTGGGCACCCGTGGTCCTGTGGTGTCTCACTGGCAGCTCAGCCTCCCG
              730       740       750       760       770       780

670       680       690       700       710       720
INSP00  TCGACGGGTGAAGATATCCACCATGCTGATCGAGGGGTGTCACTGCAGCCCAAAAGCATG
        ::::::::::::::::::::::::::::::::::::::::::::::::::::::::::::
BC0253  TCGACGGGTGAAGATATCCACCATGCTGATCGAGGGGTGTCACTGCAGCCCAAAAGCATG
              790       800       810       820       830       840

INSP00  A-----------------------------------------------------------
        :
BC0253  AACTGAGCATCTGGATGGGTGCACGGAGACACGCACCTTGGAGAAATGAGGGGAGATGGA
              850       860       870       880       890       900

INSP00  ------------------------------------------------------------
BC0253  CCAAGAAAGACGTGGACCTGGATGATGTACTCTGGGTCAAGAGACCAGGGATGCAGGGTT
              910       920       930       940       950       960

INSP00  ------------------------------------------------------------
BC0253  AGGCAGACAGGTCCCCAGAGTCCTCACCCTGCTCCCCAGACAGTAGACACAGTGCCCGTC
              970       980       990      1000      1010      1020

INSP00  ------------------------------------------------------------
BC0253  CTGGAGTTGCACCACTGATAGTCACAGCACACAATGATTGACAACTCACTTTTTTTTTTT
             1030      1040      1050      1060      1070      1080

INSP00  ------------------------------------------------------------
BC0253  TTTTTGAGATGGAGTCTCGCTCTGTCGCCCAGGCTGGAGTGCAGTGGCGCAATCTCAGCT
             1090      1100      1110      1120      1130      1140

INSP00  ------------------------------------------------------------
BC0253  CACTGCAAGCTCCACCTCCCGGGTTTATGCCATTCTCCTGTCTCAGCCTCCCGAGTAGCT
             1150      1160      1170      1180      1190      1200

INSP00  ------------------------------------------------------------
BC0253  GGGACTACAGGCACCCGCCAACACGCCCGGCTAATTTTTTGTATTTTTAGTAAAGACAGG
             1210      1220      1230      1240      1250      1260

INSP00  ------------------------------------------------------------
BC0253  GTTTCACCGTGTTAGCCAGGATGGTCTCTATCTCCTGACCTCGTGATCTGCCTGCCTTGG
             1270      1280      1290      1300      1310      1320

INSP00  ------------------------------------------------------------
BC0253  CCTTATTATTTTTTTTTTTAAGGACAGAGTCTCTCTCTGTCACCCAGGCTGGAGTGCAATG
             1330      1340      1350      1360      1370      1380
```

Figure 11a continued

```
INSP00    ---------------------------------------------------------------
BC0253    GCGCGATCTTGGCTCACTGTAACTTCCACTTGCCAGGCTCAAGCAGTTCTCCTGCCTCAG
              1390      1400      1410      1420      1430      1440

INSP00    ---------------------------------------------------------------
BC0253    CCTCCTGAGTAGCTGGGACTACAGGCACCCGCCACCATGCCCAGCTAATTTTTGTATTTT
              1450      1460      1470      1480      1490      1500

INSP00    ---------------------------------------------------------------
BC0253    TAGTAGAGACAGAGTTTCACCATATTAGCCTGGCTGGTCTCAAACTCCTGGCCTCAGGTG
              1510      1520      1530      1540      1550      1560

INSP00    ---------------------------------------------------------------
BC0253    ATCTGCCCACCTCGGCCTCCCAAAGTGCTGGGATCAAATCCACTGTTAATCATTAGGCTG
              1570      1580      1590      1600      1610      1620

INSP00    ---------------------------------------------------------------
BC0253    AACTGTCTCTTATAGAATGAGGTCAAAGACACTCCCAGTTGCAGGGAGGGTAGATGGCCC
              1630      1640      1650      1660      1670      1680

INSP00    ---------------------------------------------------------------
BC0253    CACCCAGACCGAGAGACACAGTGATGACCTCAGCCTAGGGACACCAAAAAAAAAAAAAAA
              1690      1700      1710      1720      1730      1740

INSP00    ------
BC0253    AAAAAA
```

Figure 11b: Protein sequences

```
4558384_OR    MLLGQLSTLLCLLSGALPTGSGRPEPQSPRPQSWAAANQTWALGPGALPPLVPASALGSW
INSP002_PR    MLLGQLSTLLCLLSGALPTGSGRPEPQSPRPQSWAAANQTWALGPGALPPLVPASALGSW
              ************************************************************

4558384_OR    KAFLGLQKARQLGMGRLQRGQDEVAAVTLPLNPQEVIQGMCKAVPFVQTRE---------
INSP002_PR    KAFLGLQKARQLGMGRLQRGQDEVAAVTLPLNPQEVIQGMCKAVPFVQVFSRPGCSAIRL
              ************************************************

4558384_OR    ----------SRYVAQAS---LELLASSNPP--------------TSAS-----------
INSP002_PR    RNHLCFGHCSSLYIPGSDPTPLVLCNSCMPARKRWAPVVLWCLTGSSASRRRVKISTMLI
                        * *        * * * *                  ***

4558384_OR    ---------
INSP002_PR    EGCHCSPKA
```

Figure 12 : Nucleotide sequence and translation of INSP002V generated by PCR from Image 4558384

```
  1  GTCGACTGCT AGTGACCTTG AGCCCAGTCC GGACAGACAG ACAGGCAGAC AGACGCACGG
 61  ACAAGCAGAT GCTCCTTGGC CAGCTATCCA CTCTTCTGTG CCTGCTTAGC GGGGCCCTGC
                 m  l  l  g  q  l  s  t  l  l  c  l  l  s  g  a  l
121  CTACAGGCTC AGGGAGGCCT GAACCCCAGT CTCCTCGACC TCAGTCCTGG GCTGCAGCCA
     p  t  g  s  g  r  p  e  p  q  s  p  r  p  q  s  w  a  a  a
181  ATCAGACCTG GGCTCTGGGC CCAGGGGCCC TGCCCCCACT GGTGCCAGCT TCTGCCCTTG
     n  q  t  w  a  l  g  p  g  a  l  p  p  l  v  p  a  s  a  l
241  GGAGCTGGAA GGCCTTCTTG GGCCTGCAGA AAGCCAGGCA GCTGGGGATG GGCAGGCTGC
     g  s  w  k  a  f  l  g  l  q  k  a  r  q  l  g  m  g  r  l
301  AGCGTGGGCA AGACGAGGTG GCTGCTGTGA CTCTGCCGCT GAACCCTCAG GAAGTGATCC
     q  r  g  q  d  e  v  a  a  v  t  l  p  l  n  p  q  e  v  i
361  AGGGGATGTG TAAGGCTGTG CCCTTCGTTC TCTCCCGGCC CGGCTGCTCA GCCATACGCC
     q  g  m  c  k  a  v  p  f  v  l  s  r  p  g  c  s  a  i  r
421  TCCGAAATCA TCTGTGCTTT GGTCATTGCT CCTCTCTCTA CATCCCTGGC TCGGACCCCA
     l  r  n  h  l  c  f  g  h  c  s  s  l  y  i  p  g  s  d  p
481  CCCCACTAGT CCTGTGCAAC AGCTGTATGC CTGCTCGCAA GCGTTGGGCA CCCGTGGTCC
     t  p  l  v  l  c  n  s  c  m  p  a  r  k  r  w  a  p  v  v
541  TGTGGTGTCT CACTGGCAGC TCAGCCTCCC GTCGACGGGT GAAGATATCC ACCATGCTGA
     l  w  c  l  t  g  s  s  a  s  r  r  r  v  k  i  s  t  m  l
601  TCGAGGGGTG TCACTGCAGC CCAAAAGCAT GAACTGAGCA TCTGGATGGG TGCACGGAGA
     i  e  g  c  h  c  s  p  k  a
661  CACGCACCTT GGAGAAATGA GGGGAGATGG ACCAAGAAAG ACGTGGACCT GGATGATGT
```

Figure 13: Map of pCR4blunt-TOPO-INSP002V

```
Molecule:      pCR4 blunt TOPO INSP002V,  4676 bps DNA Circular
File Name:     pCR4 blunt TOPO INSP002V.cm5
Description:   Ligation of INSP002 nestFR product into pCR4Blunt-TOPO
Notes:         plasmid ID 13075

Molecule Features:

Type      Start    End    Name          Description

REGION        2    216                  lac promoter region
REGION      205    221                  M13 reverse primimg site
REGION      217    294                  LacZa-ccdB gene fusion'
MARKER      243           T3
REGION      262    294                  Polylinker'
REGION      294    294                  TOPO cloning site'
REGION      295   1013                  INSP002V PCR product
GENE        363    923    INSP002V ORF
REGION     1014   1529                  'LacZa-ccdB gene fusion
REGION     1014   1031                  'Polylinker
REGION     1014   1014                  'TOPO cloning site
MARKER     1066         C T7
REGION     1089   1074 C                -20M13 forward priming site
GENE       1878   2672    KanR
REGION     2864   2868                  Ribosome binding site
GENE       2876   3736    AmpR
REGION     3881   4554                  pUC origin
```

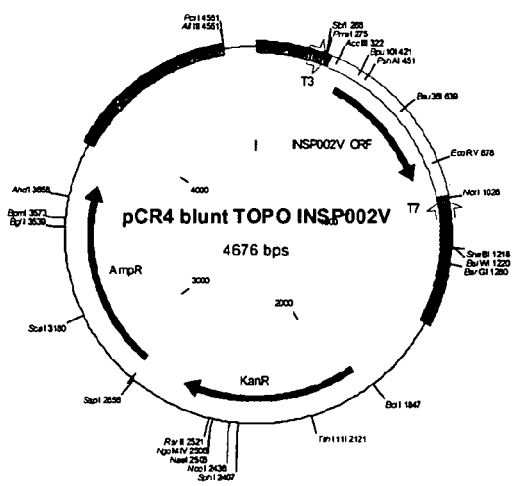

Figure 14: Comparison between INSP002 Prediction (top) and INSP002V Variant sequence (bottom)

Figure 14a: Nucleotide sequences

```
INSPpr  CAGAAATGCCTCCCAGGCTATCCAGGAGGGGCCAAGAGATTAAAAGCAGGTTCAGAAGGC

INSPen  ------------------------------------------------------------

70        80        90       100       110       120
INSPpr  TCAGATGCCACTCACCAGACAGCAGGGTCGACTGCTAGTGACCTTGAGCCCAGTCCGGAC
                                 ::::::::::::::::::::::::::::::::::
INSPen  -----------------------GTCGACTGCTAGTGACCTTGAGCCCAGTCCGGAC
                                         10        20        30

130       140       150       160       170       180
INSPpr  AGACAGACAGGCAGACAGACGCACGGACAAGCAGATGCTCCTTGGCCAGCTATCCACTCT
        ::::::::::::::::::::::::::::::::::::::::::::::::::::::::::::
INSPen  AGACAGACAGGCAGACAGACGCACGGACAAGCAGATGCTCCTTGGCCAGCTATCCACTCT
               40        50        60        70        80        90

190       200       210       220       230       240
INSPpr  TCTGTGCCTGCTTAGCGGGGCCCTGCCTACAGGCTCAGGGAGGCCTGAACCCCAGTCTCC
        ::::::::::::::::::::::::::::::::::::::::::::::::::::::::::::
INSPen  TCTGTGCCTGCTTAGCGGGGCCCTGCCTACAGGCTCAGGGAGGCCTGAACCCCAGTCTCC
              100       110       120       130       140       150

250       260       270       280       290       300
INSPpr  TCGACCTCAGTCCTGGGCTGCAGCCAATCAGACCTGGGCTCTGGGCCCAGGGGCCCTGCC
        ::::::::::::::::::::::::::::::::::::::::::::::::::::::::::::
INSPen  TCGACCTCAGTCCTGGGCTGCAGCCAATCAGACCTGGGCTCTGGGCCCAGGGGCCCTGCC
              160       170       180       190       200       210

310       320       330       340       350       360
INSPpr  CCCACTGGTGCCAGCTTCTGCCCTTGGGAGCTGGAAGGCCTTCTTGGGCCTGCAGAAAGC
        ::::::::::::::::::::::::::::::::::::::::::::::::::::::::::::
INSPen  CCCACTGGTGCCAGCTTCTGCCCTTGGGAGCTGGAAGGCCTTCTTGGGCCTGCAGAAAGC
              220       230       240       250       260       270

370       380       390       400       410       420
INSPpr  CAGGCAGCTGGGGATGGGCAGGCTGCAGCGTGGGCAAGACGAGGTGGCTGCTGTGACTCT
        ::::::::::::::::::::::::::::::::::::::::::::::::::::::::::::
INSPen  CAGGCAGCTGGGGATGGGCAGGCTGCAGCGTGGGCAAGACGAGGTGGCTGCTGTGACTCT
              280       290       300       310       320       330
```

Figure 14a continued

```
            430        440        450        460        470        480
INSPpr  GCCGCTGAACCCTCAGGAAGTGATCCAGGGGATGTGTAAGGCTGTGCCCTTCGTTCAGGT
        ::::::::::::::::::::::::::::::::::::::::::::::::::::::::
INSPen  GCCGCTGAACCCTCAGGAAGTGATCCAGGGGATGTGTAAGGCTGTGCCCTTCGTTC----
            340        350        360        370        380        390

490        500        510        520        530        540
INSPpr  GTTCTCCCGGCCCGGCTGCTCAGCCATACGCCTCCGAAATCATCTGTGCTTTGGTCATTG
          ::::::::::::::::::::::::::::::::::::::::::::::::::::::::
INSPen  --TCTCCCGGCCCGGCTGCTCAGCCATACGCCTCCGAAATCATCTGTGCTTTGGTCATTG
            400        410        420        430        440

550        560        570        580        590        600
INSPpr  CTCCTCTCTCTACATCCCTGGCTCGGACCCCACCCCACTAGTCCTGTGCAACAGCTGTAT
        ::::::::::::::::::::::::::::::::::::::::::::::::::::::::::::
INSPen  CTCCTCTCTCTACATCCCTGGCTCGGACCCCACCCCACTAGTCCTGTGCAACAGCTGTAT
            450        460        470        480        490        500

610        620        630        640        650        660
INSPpr  GCCTGCTCGCAAGCGTTGGGCACCCGTGGTCCTGTGGTGTCTCACTGGCAGCTCAGCCTC
        ::::::::::::::::::::::::::::::::::::::::::::::::::::::::::::
INSPen  GCCTGCTCGCAAGCGTTGGGCACCCGTGGTCCTGTGGTGTCTCACTGGCAGCTCAGCCTC
            510        520        530        540        550        560

670        680        690        700        710        720
INSPpr  CCGTCGACGGGTGAAGATATCCACCATGCTGATCGAGGGGTGTCACTGCAGCCCAAAAGC
        ::::::::::::::::::::::::::::::::::::::::::::::::::::::::::::
INSPen  CCGTCGACGGGTGAAGATATCCACCATGCTGATCGAGGGGTGTCACTGCAGCCCAAAAGC
            570        580        590        600        610        620

INSPpr  ATGA--------------------------------------------------------
        ::::
INSPen  ATGAACTGAGCATCTGGATGGGTGCACGGAGACACGCACCTTGGAGAAATGAGGGGAGAT
            630        640        650        660        670        680

INSPpr  ------------------------

INSPen  GGACCAAGAAAGACGTGGACCTGGATGATGT
            690        700        710
```

Figure 14b: Protein sequences

```
INSP002V     23 MLLGQLSTLLCLLSGALPTGSGRPEPQSPRPQSWAAANQTWALGPGALPPLVPASALGSW
INSP002       1 MLLGQLSTLLCLLSGALPTGSGRPEPQSPRPQSWAAANQTWALGPGALPPLVPASALGSW
                ************************************************************

INSP002V     83 KAFLGLQKARQLGMGRLQRGQDEVAAVTLPLNPQEVIQGMCKAVPF--VLSRPGCSAIRL
INSP002      61 KAFLGLQKARQLGMGRLQRGQDEVAAVTLPLNPQEVIQGMCKAVPFVQVFSRPGCSAIRL
                **********************************************  * *********

INSP002V    141 RNHLCFGHCSSLYIPGSDPTPLVLCNSCMPARKRWAPVVLWCLTGSSASRRRVKISTMLI
INSP002     121 RNHLCFGHCSSLYIPGSDPTPLVLCNSCMPARKRWAPVVLWCLTGSSASRRRVKISTMLI
                ************************************************************

INSP002V    201 EGCHCSPKA
INSP002     181 EGCHCSPKA
                *********
```

Figure 15: Map of expression vector pEAK12d

```
Molecule:    pEAK12 d, 8760 bps DNA Circular
File Name:   pEAK12DEST.cm5

Description: Mammalian cell expression vector (plasmid ID 11345)

Molecule Features:
```

| Type | Start | End | | Name | Description |
|---|---|---|---|---|---|
| REGION | 2 | 595 | | | pmb-ori |
| GENE | 596 | 1519 | | Amp | |
| REGION | 1690 | 2795 | | EF-1alpha | |
| REGION | 2703 | 2722 | | | position of pEAK12F primer |
| REGION | 2796 | 2845 | | | MCS |
| MARKER | 2855 | | | attR1 | |
| GENE | 3256 | 3915 | | CmR | |
| GENE | 4257 | 4562 | | ccdB | |
| MARKER | 4603 | | C | attR2 | |
| REGION | 4733 | 4733 | | | MCS |
| REGION | 4734 | 5162 | | | poly A/splice |
| REGION | 4819 | 4848 | C | | position of pEAK12R primer |
| GENE | 5781 | 5163 | C | PUR | PUROMYCIN |
| REGION | 6005 | 5782 | C | tK | tK promoter |
| REGION | 6500 | 6006 | C | Ori P | |
| GENE | 8552 | 6500 | C | EBNA-1 | |
| REGION | 8553 | 8752 | | sv40 | |

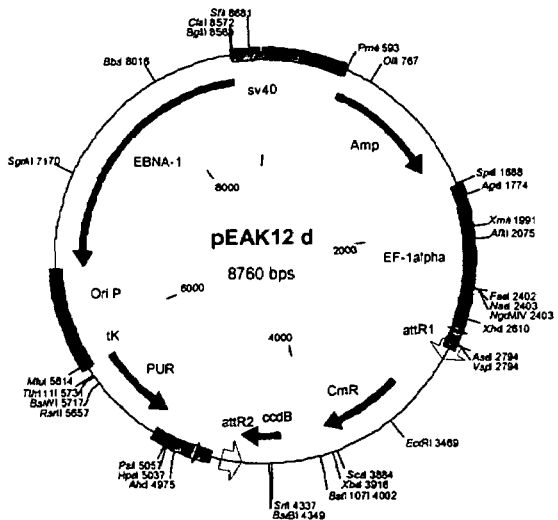

Figure 16: Map of Gateway vector pDONR201
```
Molecule:      pDONR201,  4470 bps DNA Circular
File Name:     pDONR201.cm5
Description:   Gateway entry vector (Invitrogen)- plasmid ID# 13309
Molecule Features:
Type      Start     End      Name
REGION    332       563      attP1
GENE      959       1264     ccdB
REGION    2513      2744     attP2
GENE      2868      3677     KanR
REGION    3794      4467     pUC ori
```
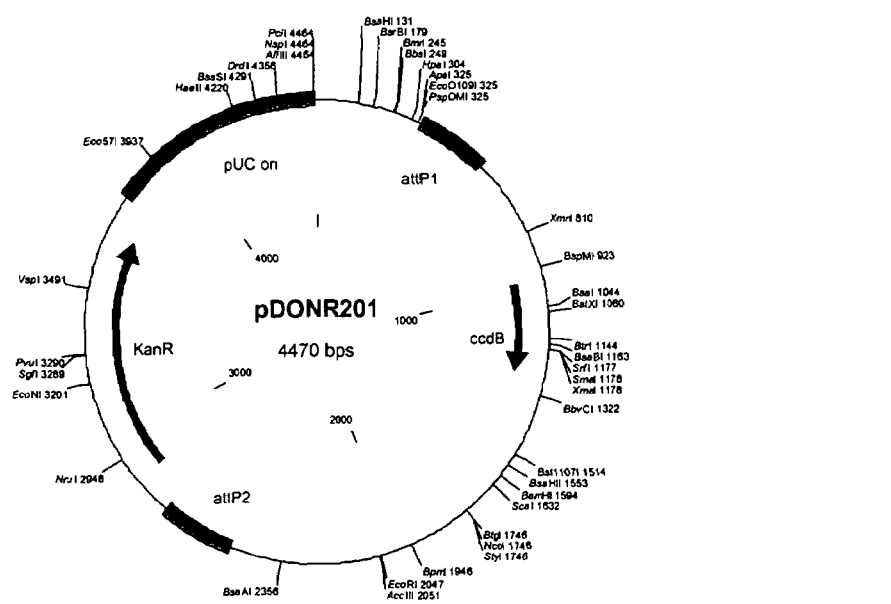

Figure 17: Map of pEAK12d-INSP002-V-6HIS

```
Molecule:     pEAK12d-INSP002-V-6HIS, 7528 bps DNA Circular
File Name:    pEAK12d-INSP002V-6HIS.cm5
Description:  cDNA is inserted between attR1 and attR2 sites
Notes:        plasmid ID 13227
```

Molecule Features:

| Type   | Start | End  |   | Name     | Description    |
|--------|-------|------|---|----------|----------------|
| REGION | 2     | 595  |   |          | pmb-ori        |
| GENE   | 596   | 1519 |   | AmpR     |                |
| REGION | 1690  | 2795 |   | EF-1alpha| promoter       |
| REGION | 2703  | 2722 |   |          | pEAK12F        |
| REGION | 2796  | 2845 |   |          | MCS''          |
| REGION | 2855  | 2874 |   |          | attB1          |
| GENE   | 2888  | 3469 |   | INSP002-V|                |
| REGION | 3474  | 3495 |   |          | attB2          |
| REGION | 3501  | 3501 |   |          | 'MCS           |
| REGION | 3502  | 3930 |   |          | poly A/splice  |
| REGION | 3616  | 3597 | C |          | pEAK12R        |
| GENE   | 4549  | 3931 | C |          | PUROMYCIN R    |
| REGION | 4773  | 4550 | C |          | tK promoter    |
| REGION | 5268  | 4774 | C | Ori P    |                |
| GENE   | 7320  | 5268 | C | EBNA-1   |                |
| REGION | 7321  | 7520 |   | sv40     |                |

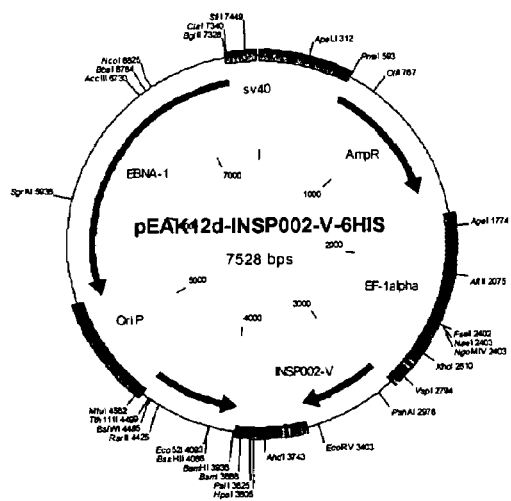

Figure 18: Full length INSP002 cloned from human heart cDNA

```
  1  GATGCTCCTT GGCCAGCTAT CCACTCTTCT GTGCCTGCTT AGCGGGGCCC TGCCTACAGG
      m  l  l    g  q  I    s  t  l    l  c  l    l  s  g  a    l  p  t
        INSP002-FL-F

61  CTCAGGGAGG CCTGAACCCC AGTCTCCTCG ACCTCAGTCC TGGGCTGCAG CCAATCAGAC
      g  s  g  r    p  e  p    q  s  p    r  p  q  s    w  a  a    n  q

121  CTGGGCTCTG GGCCCAGGGG CCCTGCCCCC ACTGGTGCCA GCTTCTGCCC TTGGGAGCTG
      t  w  a  l    g  p  g    a  l  p    p  l  v  p    a  s    l  g  s

181  GAAGGCCTTC TTGGGCCTGC AGAAAGCCAG GCAGCTGGGG ATGGGCAGGC TGCAGCGTGG
      w  k  a  f    l  g  l    q  k  a    r  q  l  g    m  g  r    l  q  r

241  GCAAGACGAG GTGGCTGCTG TGACTCTGCC GCTGAACCCT CAGGAAGTGA TCCAGGGGAT
      g  q  d  e    v  a  a    v  t  l    p  l  n  p    q  e  v    i  q  g

301  GTGTAAGGCT GTGCCCTTCG TTCAGGTGTT CTCCCGGCCC GGCTGCTCAG CCATACGCCT
      m  c  k  a    v  p  f    v  q  v    f  s  r  p    g  c  s    a  i  r

361  CCGAAATCAT CTGTGCTTTG GTCATTGCTC CTCTCTCTAC ATCCCTGGCT CGGACCCCAC
      l  r  n  h    l  c  f    g  h  c    s  s  l  y    i  p  g    s  d  p

421  CCCACTAGTC CTGTGCAACA GCTGTATGCC TGCTCGCAAG CGTTGGGCAC CCGTGGTCCT
      t  p  l  v    l  c  n    s  c  m    p  a  r  k    r  w  a    p  v  v

481  GTGGTGTCTC ACTGGCAGCT CAGCCTCCCG TCGACGGGTG AAGATATCCA CCATGCTGAT
      l  w  c  l    t  g  s    s  a  s    r  r  v  k    i  s    t  m  l

541  CGAGGGGTGT CACTGCAGCC CAAAAGCATG AACTGAGCAT CGTGGATGG
      i  e  g  c    h  c  s    p  k  a
                                        INSP002-FL-R
```

Figure 19: Map of PCR4blunt-TOPO-INSP002FL

```
Molecule:      pCR4blunt TOPO INSP002FL,  4546 bps DNA Circular
File Name:     pCR4 blunt TOPO INSP002 FL.cm5,
Description:   Ligation of NoName into pCR4Blunt-TOPO open*

Molecule Features:

Type      Start    End    Name       Description

REGION       2     216               lac promoter region
REGION     205     221               M13 reverse primimg site
REGION     217     294               LacZa-ccdB gene fusion
MARKER     243            T3
REGION     262     294               Polylinker
REGION     294     294               TOPO cloning site
REGION     295     883               INSP002-F3R3 PCR product
GENE       296     865    INSP002    INSP002 ORF
REGION     884    1399               'LacZa-ccdB gene fusion
REGION     884     901               Polylinker
REGION     884     884               'TOPO cloning site
MARKER     936         C  T7         T7promoter
REGION     959     944  C            -20M13 forward priming site
GENE      1748    2542    KanR       Kanamycin resistance gene ORF
REGION    2734    2738               Ribosome binding site
GENE      2746    3606    AmpR       Ampicillin resistance gene ORF
REGION    3751    4424    pUC ori    pUC origin
```

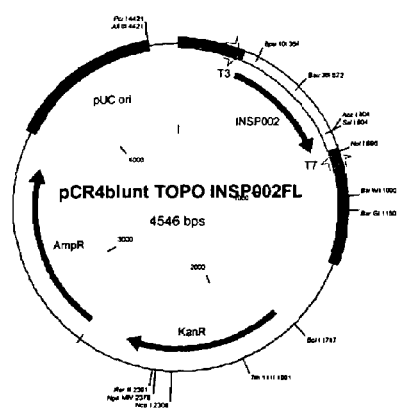

SEQUENCE LISTING

```
<160> NUMBER OF SEQ ID NOS: 38

<210> SEQ ID NO 1
<211> LENGTH: 475
<212> TYPE: DNA
<213> ORGANISM: Homo sapiens
<220> FEATURE:
<221> NAME/KEY: INSP002 Nucleotide sequence - Exon 1

<400> SEQUENCE: 1
aaatgcctcc caggctatcc aggaggggcc aagagattaa aagcaggttc agaaggctca      60
gatgccactc accagacagc agggtcgact gctagtgacc ttgagcccag tccggacaga     120
cagacaggca gacagacgca cggacaagca gatgctcctt ggccagctat ccactcttct     180
```

```
gtgcctgctt agcggggccc tgcctacagg ctcaggagg cctgaacccc agtctcctcg      240
acctcagtcc tgggctgcag ccaatcagac ctgggctctg ggcccagggg ccctgccccc      300
actggtgcca gcttctgccc ttgggagctg aaggccttc ttgggcctgc agaaagccag       360
gcagctgggg atgggcaggc tgcagcgtgg gcaagacgag gtggctgctg tgactctgcc      420
gctgaaccct caggaagtga tccagggat gtgtaaggct gtgcccttcg ttcag           475

<210> SEQ ID NO 2
<211> LENGTH: 108
<212> TYPE: PRT
<213> ORGANISM: Homo sapiens
<220> FEATURE:
<221> NAME/KEY: INSP002 Protein sequence - Exon 1

<400> SEQUENCE: 2

Met Leu Leu Gly Gln Leu Ser Thr Leu Leu Cys Leu Ser Gly Ala
1               5                   10                  15

Leu Pro Thr Gly Ser Gly Arg Pro Glu Pro Gln Ser Pro Arg Pro Gln
                20                  25                  30

Ser Trp Ala Ala Ala Asn Gln Thr Trp Ala Leu Gly Pro Gly Ala Leu
            35                  40                  45

Pro Pro Leu Val Pro Ala Ser Ala Leu Gly Ser Trp Lys Ala Phe Leu
        50                  55                  60

Gly Leu Gln Lys Ala Arg Gln Leu Gly Met Gly Arg Leu Gln Arg Gly
65                  70                  75                  80

Gln Asp Glu Val Ala Ala Val Thr Leu Pro Leu Asn Pro Gln Glu Val
                85                  90                  95

Ile Gln Gly Met Cys Lys Ala Val Pro Phe Val Gln
            100                 105

<210> SEQ ID NO 3
<211> LENGTH: 246
<212> TYPE: DNA
<213> ORGANISM: Homo sapiens
<220> FEATURE:
<221> NAME/KEY: INSP002 Nucleotide sequence - Exon 2

<400> SEQUENCE: 3
gtgttctccc ggcccggctg ctcagccata cgcctccgaa atcatctgtg ctttggtcat       60
tgctcctctc tctacatccc tggctcggac cccacccca tagtcctgtg caacagctgt       120
atgcctgctc gcaagcgttg ggcacccgtg gtcctgtggt gtctcactgg cagctcagcc      180
tcccgtcgac gggtgaagat atccaccatg ctgatcgagg ggtgtcactg cagcccaaaa      240
gcatga                                                                 246

<210> SEQ ID NO 4
<211> LENGTH: 81
<212> TYPE: PRT
<213> ORGANISM: Homo sapiens
<220> FEATURE:
<221> NAME/KEY: INSP002 Protein sequence - Exon 2

<400> SEQUENCE: 4

Val Phe Ser Arg Pro Gly Cys Ser Ala Ile Arg Leu Arg Asn His Leu
1               5                   10                  15

Cys Phe Gly His Cys Ser Ser Leu Tyr Ile Pro Gly Ser Asp Pro Thr
                20                  25                  30

Pro Leu Val Leu Cys Asn Ser Cys Met Pro Ala Arg Lys Arg Trp Ala
            35                  40                  45
```

```
Pro Val Val Leu Trp Cys Leu Thr Gly Ser Ser Ala Ser Arg Arg Arg
    50                  55                  60

Val Lys Ile Ser Thr Met Leu Ile Glu Gly Cys His Cys Ser Pro Lys
65                  70                  75                  80

Ala

<210> SEQ ID NO 5
<211> LENGTH: 721
<212> TYPE: DNA
<213> ORGANISM: Homo sapiens
<220> FEATURE:
<221> NAME/KEY: INSP002 - Nucleotide sequence

<400> SEQUENCE: 5
aaatgcctcc caggctatcc aggaggggcc aagagattaa agcaggttc agaaggctca      60
gatgccactc accagacagc agggtcgact gctagtgacc ttgagcccag tccggacaga    120
cagacaggca gacagacgca cggacaagca gatgctcctt ggccagctat ccactcttct    180
gtgcctgctt agcggggccc tgcctacagg ctcaggagg cctgaacccc agtctcctcg    240
acctcagtcc tgggctgcag ccaatcagac ctgggctctg ggcccagggg ccctgccccc    300
actggtgcca gcttctgccc ttgggagctg gaaggccttc ttgggcctgc agaaagccag    360
gcagctgggg atgggcaggc tgcagcgtgg caagacgag gtggctgctg tgactctgcc    420
gctgaaccct caggaagtga tccaggggat gtgtaaggct gtgcccttcg ttcaggtgtt    480
ctcccggccc ggctgctcag ccatacgcct ccgaaatcat ctgtgctttg gtcattgctc    540
ctctctctac atccctggct cggaccccac cccactagtc ctgtgcaaca gctgtatgcc    600
tgctcgcaag cgttgggcac ccgtggtcct gtggtgtctc actggcagct cagcctcccg    660
tcgacgggtg aagatatcca ccatgctgat cgaggggtgt cactgcagcc aaaagcatg    720
a                                                                   721

<210> SEQ ID NO 6
<211> LENGTH: 189
<212> TYPE: PRT
<213> ORGANISM: Homo sapiens
<220> FEATURE:
<221> NAME/KEY: INSP002 Protein sequence

<400> SEQUENCE: 6

Met Leu Leu Gly Gln Leu Ser Thr Leu Leu Cys Leu Leu Ser Gly Ala
1               5                   10                  15

Leu Pro Thr Gly Ser Gly Arg Pro Glu Pro Gln Ser Pro Arg Pro Gln
            20                  25                  30

Ser Trp Ala Ala Ala Asn Gln Thr Trp Ala Leu Gly Pro Gly Ala Leu
        35                  40                  45

Pro Pro Leu Val Pro Ala Ser Ala Leu Gly Ser Trp Lys Ala Phe Leu
    50                  55                  60

Gly Leu Gln Lys Ala Arg Gln Leu Gly Met Gly Arg Leu Gln Arg Gly
65                  70                  75                  80

Gln Asp Glu Val Ala Ala Val Thr Leu Pro Leu Asn Pro Gln Glu Val
                85                  90                  95

Ile Gln Gly Met Cys Lys Ala Val Pro Phe Val Gln Val Phe Ser Arg
            100                 105                 110

Pro Gly Cys Ser Ala Ile Arg Leu Arg Asn His Leu Cys Phe Gly His
        115                 120                 125
```

```
Cys Ser Ser Leu Tyr Ile Pro Gly Ser Asp Pro Thr Pro Leu Val Leu
        130                 135                 140

Cys Asn Ser Cys Met Pro Ala Arg Lys Arg Trp Ala Pro Val Val Leu
145                 150                 155                 160

Trp Cys Leu Thr Gly Ser Ser Ala Ser Arg Arg Val Lys Ile Ser
                165                 170                 175

Thr Met Leu Ile Glu Gly Cys His Cys Ser Pro Lys Ala
            180                 185

<210> SEQ ID NO 7
<211> LENGTH: 86
<212> TYPE: PRT
<213> ORGANISM: Homo sapiens
<220> FEATURE:
<221> NAME/KEY: INSP002 Protein sequence - Exon 1 without signal peptide

<400> SEQUENCE: 7

Arg Pro Glu Pro Gln Ser Pro Arg Pro Gln Ser Trp Ala Ala Ala Asn
1               5                   10                  15

Gln Thr Trp Ala Leu Gly Pro Gly Ala Leu Pro Pro Leu Val Pro Ala
            20                  25                  30

Ser Ala Leu Gly Ser Trp Lys Ala Phe Leu Gly Leu Gln Lys Ala Arg
        35                  40                  45

Gln Leu Gly Met Gly Arg Leu Gln Arg Gly Gln Asp Glu Val Ala Ala
    50                  55                  60

Val Thr Leu Pro Leu Asn Pro Gln Glu Val Ile Gln Gly Met Cys Lys
65                  70                  75                  80

Ala Val Pro Phe Val Gln
                85

<210> SEQ ID NO 8
<211> LENGTH: 167
<212> TYPE: PRT
<213> ORGANISM: Homo sapiens
<220> FEATURE:
<221> NAME/KEY: INSP002 Protein sequence without signal peptide

<400> SEQUENCE: 8

Arg Pro Glu Pro Gln Ser Pro Arg Pro Gln Ser Trp Ala Ala Ala Asn
1               5                   10                  15

Gln Thr Trp Ala Leu Gly Pro Gly Ala Leu Pro Pro Leu Val Pro Ala
            20                  25                  30

Ser Ala Leu Gly Ser Trp Lys Ala Phe Leu Gly Leu Gln Lys Ala Arg
        35                  40                  45

Gln Leu Gly Met Gly Arg Leu Gln Arg Gly Gln Asp Glu Val Ala Ala
    50                  55                  60

Val Thr Leu Pro Leu Asn Pro Gln Glu Val Ile Gln Gly Met Cys Lys
65                  70                  75                  80

Ala Val Pro Phe Val Gln Val Phe Ser Arg Pro Gly Cys Ser Ala Ile
                85                  90                  95

Arg Leu Arg Asn His Leu Cys Phe Gly His Cys Ser Ser Leu Tyr Ile
            100                 105                 110

Pro Gly Ser Asp Pro Thr Pro Leu Val Leu Cys Asn Ser Cys Met Pro
        115                 120                 125

Ala Arg Lys Arg Trp Ala Pro Val Val Leu Trp Cys Leu Thr Gly Ser
    130                 135                 140

Ser Ala Ser Arg Arg Val Lys Ile Ser Thr Met Leu Ile Glu Gly
145                 150                 155                 160
```

Cys His Cys Ser Pro Lys Ala
            165

<210> SEQ ID NO 9
<211> LENGTH: 504
<212> TYPE: DNA
<213> ORGANISM: Homo sapiens
<220> FEATURE:
<221> NAME/KEY: INSP002 Nucleotide sequence - without signal peptide

<400> SEQUENCE: 9

| | | | | | |
|---|---|---|---|---|---|
| aggcctgaac | cccagtctcc | tcgacctcag | tcctgggctg | cagccaatca | gacctgggct | 60 |
| ctgggcccag | gggccctgcc | cccactggtg | ccagcttctg | cccttgggag | ctggaaggcc | 120 |
| ttcttgggcc | tgcagaaagc | caggcagctg | gggatgggca | ggctgcagcg | tgggcaagac | 180 |
| gaggtggctg | ctgtgactct | gccgctgaac | cctcaggaag | tgatccaggg | gatgtgtaag | 240 |
| gctgtgccct | tcgttcaggt | gttctcccgg | cccggctgct | cagccatacg | cctccgaaat | 300 |
| catctgtgct | ttggtcattg | ctcctctctc | tacatccctg | gctcggaccc | caccccacta | 360 |
| gtcctgtgca | acagctgtat | gcctgctcgc | aagcgttggg | cacccgtggt | cctgtggtgt | 420 |
| ctcactggca | gctcagcctc | ccgtcgacgg | gtgaagatat | ccaccatgct | gatcgagggg | 480 |
| tgtcactgca | gcccaaaagc | atga | | | | 504 |

<210> SEQ ID NO 10
<211> LENGTH: 258
<212> TYPE: DNA
<213> ORGANISM: Homo sapiens
<220> FEATURE:
<221> NAME/KEY: INSP002 Nucleotide sequence - Exon 1 without signal
      peptide

<400> SEQUENCE: 10

| | | | | | |
|---|---|---|---|---|---|
| aggcctgaac | cccagtctcc | tcgacctcag | tcctgggctg | cagccaatca | gacctgggct | 60 |
| ctgggcccag | gggccctgcc | cccactggtg | ccagcttctg | cccttgggag | ctggaaggcc | 120 |
| ttcttgggcc | tgcagaaagc | caggcagctg | gggatgggca | ggctgcagcg | tgggcaagac | 180 |
| gaggtggctg | ctgtgactct | gccgctgaac | cctcaggaag | tgatccaggg | gatgtgtaag | 240 |
| gctgtgccct | tcgttcag | | | | | 258 |

<210> SEQ ID NO 11
<211> LENGTH: 570
<212> TYPE: DNA
<213> ORGANISM: Homo sapiens
<220> FEATURE:
<221> NAME/KEY: INSP002 Nucleotide sequence - without 5' UTR

<400> SEQUENCE: 11

| | | | | | |
|---|---|---|---|---|---|
| atgctccttg | gccagctatc | cactcttctg | tgcctgctta | gcggggccct | gcctacaggc | 60 |
| tcagggaggc | ctgaacccca | gtctcctcga | cctcagtcct | gggctgcagc | caatcagacc | 120 |
| tgggctctgg | gccagggggc | cctgccccca | ctggtgccag | cttctgccct | tgggagctgg | 180 |
| aaggccttct | tgggcctgca | gaaagccagg | cagctgggga | tgggcaggct | gcagcgtggg | 240 |
| caagacgagg | tggctgctgt | gactctgccg | ctgaaccctc | aggaagtgat | ccaggggatg | 300 |
| tgtaaggctg | tgcccttcgt | tcaggtgttc | tccggcccg | gctgctcagc | catacgcctc | 360 |
| cgaaatcatc | tgtgctttgg | tcattgctc | tctctctaca | tccctggctc | ggaccccacc | 420 |
| ccactagtcc | tgtgcaacag | ctgtatgcct | gctcgcaagc | gttgggcacc | cgtggtcctg | 480 |

```
tggtgtctca ctggcagctc agcctcccgt cgacgggtga agatatccac catgctgatc    540
gaggggtgtc actgcagccc aaaagcatga                                     570
```

<210> SEQ ID NO 12
<211> LENGTH: 324
<212> TYPE: DNA
<213> ORGANISM: Homo sapiens
<220> FEATURE:
<221> NAME/KEY: INSP002 Nucleotide sequence - exon 1 without 5' UTR

<400> SEQUENCE: 12

```
atgctccttg gccagctatc cactcttctg tgcctgctta gcggggccct gcctacaggc     60
tcagggaggc ctgaacccca gtctcctcga cctcagtcct gggctgcagc caatcagacc    120
tgggctctgg gccaggggc  cctgccccca ctggtgccag cttctgccct gggagctgg     180 aaggccttct ggggcctgca gaaagccagg cagctgggga tgggcaggct gcagcgtggg    240
caagacgagg tggctgctgt gactctgccg ctgaaccctc aggaagtgat ccaggggatg    300
tgtaaggctg tgccct tcgt tcag                                          324
```

<210> SEQ ID NO 13
<211> LENGTH: 719
<212> TYPE: DNA
<213> ORGANISM: Homo sapiens
<220> FEATURE:
<221> NAME/KEY: INSP002 Nucleotide sequence - variant INSP002
     polypeptide

<400> SEQUENCE: 13

```
gtcgactgct agtgaccttg agcccagtcc ggacagacag acaggcagac agacgcacgg     60
acaagcagat gctccttggc cagctatcca ctcttctgtg cctgcttagc ggggccctgc    120
ctacaggctc agggaggcct gaaccccagt ctcctcgacc tcagtcctgg gctgcagcca    180
atcagacctg gctctgggc  ccaggggccc tgccccact  ggtgccagct tctgcccttg    240
ggagctggaa ggccttcttg ggcctgcaga aagccaggca gctggggatg gcaggctgc     300 agcgtgggca agacgaggtg gctgctgtga ctctgccgct gaaccctcag gaagtgatcc    360
aggggatgtg taaggctgtg cccttcgttc tctcccggcc cggctgctca gccatacgcc    420
tccgaaatca tctgtgcttt ggtcattgct cctctctcta catccctggc tcgaccccca    480
ccccactagt cctgtgcaac agctgtatgc ctgctcgcaa gcgttgggca cccgtggtcc    540
tgtggtgtct cactggcagc tcagcctccc gtcgacgggt gaagatatcc accatgctga    600
tcgaggggtg tcactgcagc ccaaaagcat gaactgagca tctggatggg tgcacggaga    660
cacgcacctt ggagaaatga ggggagatgg accaagaaag acgtggacct ggatgatgt    719
```

<210> SEQ ID NO 14
<211> LENGTH: 187
<212> TYPE: PRT
<213> ORGANISM: Homo sapiens
<220> FEATURE:
<221> NAME/KEY: INSP002 Polypeptide sequence - variant INSP002
     polypeptide

<400> SEQUENCE: 14

```
Met Leu Leu Gly Gln Leu Ser Thr Leu Leu Cys Leu Leu Ser Gly Ala
1               5                   10                  15

Leu Pro Thr Gly Ser Gly Arg Pro Glu Pro Gln Ser Pro Arg Pro Gln
            20                  25                  30

Ser Trp Ala Ala Ala Asn Gln Thr Trp Ala Leu Gly Pro Gly Ala Leu
```

```
              35                  40                  45
Pro Pro Leu Val Pro Ala Ser Ala Leu Gly Ser Trp Lys Ala Phe Leu
 50                  55                  60

Gly Leu Gln Lys Ala Arg Gln Leu Gly Met Gly Arg Leu Gln Arg Gly
 65                  70                  75                  80

Gln Asp Glu Val Ala Ala Val Thr Leu Pro Leu Asn Pro Gln Glu Val
                 85                  90                  95

Ile Gly Met Cys Lys Ala Val Pro Phe Val Leu Ser Arg Pro Gly
                100                 105                 110

Cys Ser Ala Ile Arg Leu Arg Asn His Leu Cys Phe Gly His Cys Ser
                115                 120                 125

Ser Leu Tyr Ile Pro Gly Ser Asp Pro Thr Pro Leu Val Leu Cys Asn
130                 135                 140

Ser Cys Met Pro Ala Arg Lys Arg Trp Ala Pro Val Val Leu Trp Cys
145                 150                 155                 160

Leu Thr Gly Ser Ser Ala Ser Arg Arg Val Lys Ile Ser Thr Met
                165                 170                 175

Leu Ile Glu Gly Cys His Cys Ser Pro Lys Ala
                180                 185
```

<210> SEQ ID NO 15
<211> LENGTH: 561
<212> TYPE: DNA
<213> ORGANISM: Homo sapiens
<220> FEATURE:
<221> NAME/KEY: INSP002 Nucleotide sequence - INSP002 variant
      polypeptide without 5' UTR

<400> SEQUENCE: 15

```
atgctccttg gccagctatc cactcttctg tgcctgctta gcggggccct gcctacaggc        60
tcagggaggc ctgaacccca gtctcctcga cctcagtcct gggctgcagc caatcagacc       120
tgggctctgg gccaggggc cctgccccca ctggtgccag cttctgccct gggagctgg         180
aaggccttct tgggcctgca gaaagccagg cagctgggga tgggcaggct gcagcgtggg       240
caagacgagg tggctgctgt gactctgccg ctgaaccctc aggaagtgat ccaggggatg       300
tgtaaggctg tgcccttcgt tctctcccgg cccggctgct cagccatacg cctccgaaat       360
catctgtgct ttggtcattg ctcctctctc tacatccctg gctcggaccc caccccacta       420
gtcctgtgca acagctgtat gcctgctcgc aagcgttggg cacccgtggt cctgtggtgt       480
ctcactggca gctcagcctc cgtcgacgg gtgaagatat ccaccatgct gatcgagggg        540
tgtcactgca gcccaaaagc a                                                 561
```

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16

```
ctcagccata cgcctccgaa                                                    20
```

<210> SEQ ID NO 17
<211> LENGTH: 20
<212> TYPE: DNA
<213> ORGANISM: Artificial Sequence
<220> FEATURE:
<223> OTHER INFORMATION: PCR Primer

```
<400> SEQUENCE: 17
gctgagctgc cagtgagaca                                              20

<210> SEQ ID NO 18
<211> LENGTH: 25
<212> TYPE: DNA
<213> ORGANISM: Artificial Sequence
<220> FEATURE:
<223> OTHER INFORMATION: PCR Primer

<400> SEQUENCE: 18
acctggaagg aagcgactgc actga                                        25

<210> SEQ ID NO 19
<211> LENGTH: 37
<212> TYPE: DNA
<213> ORGANISM: Artificial Sequence
<220> FEATURE:
<223> OTHER INFORMATION: PCR Primer

<400> SEQUENCE: 19
gcagccgggc cgggagagaa cgaagggcac agcctta                           37

<210> SEQ ID NO 20
<211> LENGTH: 37
<212> TYPE: DNA
<213> ORGANISM: Artificial Sequence
<220> FEATURE:
<223> OTHER INFORMATION: PCR Primer

<400> SEQUENCE: 20
aggctgtgcc cttcgttctc tcccggcccg gctgctc                           37

<210> SEQ ID NO 21
<211> LENGTH: 25
<212> TYPE: DNA
<213> ORGANISM: Artificial Sequence
<220> FEATURE:
<223> OTHER INFORMATION: PCR Primer

<400> SEQUENCE: 21
actccaggac gggcactgtg tctac                                        25

<210> SEQ ID NO 22
<211> LENGTH: 22
<212> TYPE: DNA
<213> ORGANISM: Artificial Sequence
<220> FEATURE:
<223> OTHER INFORMATION: PCR Primer

<400> SEQUENCE: 22
gtcgactgct agtgaccttg ag                                           22

<210> SEQ ID NO 23
<211> LENGTH: 22
<212> TYPE: DNA
<213> ORGANISM: Artificial Sequence
<220> FEATURE:
<223> OTHER INFORMATION: PCR Primer

<400> SEQUENCE: 23
acatcatcca ggtccacgtc tt                                           22

<210> SEQ ID NO 24
```

-continued

```
<211> LENGTH: 18
<212> TYPE: DNA
<213> ORGANISM: Artificial Sequence
<220> FEATURE:
<223> OTHER INFORMATION: PCR Primer

<400> SEQUENCE: 24
atttaggtga cactatag                                                 18

<210> SEQ ID NO 25
<211> LENGTH: 20
<212> TYPE: DNA
<213> ORGANISM: Artificial Sequence
<220> FEATURE:
<223> OTHER INFORMATION: PCR Primer

<400> SEQUENCE: 25
taatacgact cactataggg                                               20

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
attaaccctc actaaaggga                                               20

<210> SEQ ID NO 27
<211> LENGTH: 18
<212> TYPE: DNA
<213> ORGANISM: Artificial Sequence
<220> FEATURE:
<223> OTHER INFORMATION: PCR Primer

<400> SEQUENCE: 27
tgtaaaacga cggccagt                                                 18

<210> SEQ ID NO 28
<211> LENGTH: 20
<212> TYPE: DNA
<213> ORGANISM: Artificial Sequence
<220> FEATURE:
<223> OTHER INFORMATION: PCR Primer

<400> SEQUENCE: 28
gccagcttgg cacttgatgt                                               20

<210> SEQ ID NO 29
<211> LENGTH: 20
<212> TYPE: DNA
<213> ORGANISM: Artificial Sequence
<220> FEATURE:
<223> OTHER INFORMATION: PCR Primer

<400> SEQUENCE: 29
gatggaggtg gacgtgtcag                                               20

<210> SEQ ID NO 30
<211> LENGTH: 37
<212> TYPE: DNA
<213> ORGANISM: Artificial Sequence
<220> FEATURE:
<223> OTHER INFORMATION: PCR Primer

<400> SEQUENCE: 30
```
aagcaggctt cgccaccatg ctccttggcc agctatc    37

<210> SEQ ID NO 31
<211> LENGTH: 35
<212> TYPE: DNA
<213> ORGANISM: Artificial Sequence
<220> FEATURE:
<223> OTHER INFORMATION: PCR Primer

<400> SEQUENCE: 31
gtgatggtga tggtgtgctt ttgggctgca gtgac    35

<210> SEQ ID NO 32
<211> LENGTH: 37
<212> TYPE: DNA
<213> ORGANISM: Artificial Sequence
<220> FEATURE:
<223> OTHER INFORMATION: PCR Primer

<400> SEQUENCE: 32
ggggacaagt ttgtacaaaa aagcaggctt cgccacc    37

<210> SEQ ID NO 33
<211> LENGTH: 51
<212> TYPE: DNA
<213> ORGANISM: Artificial Sequence
<220> FEATURE:
<223> OTHER INFORMATION: PCR Primer

<400> SEQUENCE: 33
ggggaccact ttgtacaaga aagctgggtt tcaatggtga tggtgatggt g    51

<210> SEQ ID NO 34
<211> LENGTH: 20
<212> TYPE: DNA
<213> ORGANISM: Artificial Sequence
<220> FEATURE:
<223> OTHER INFORMATION: PCR Primer

<400> SEQUENCE: 34
gatgctcctt ggccagctat    20

<210> SEQ ID NO 35
<211> LENGTH: 20
<212> TYPE: DNA
<213> ORGANISM: Artificial Sequence
<220> FEATURE:
<223> OTHER INFORMATION: PCR Primer

<400> SEQUENCE: 35
ccatccacga tgctcagttc    20

<210> SEQ ID NO 36
<211> LENGTH: 1756
<212> TYPE: DNA
<213> ORGANISM: Artificial Sequence
<220> FEATURE:
<223> OTHER INFORMATION: Vector Insert
<220> FEATURE:
<221> NAME/KEY: Sequence of vector insert containing Image 4558384
      (Figure 10)

<400> SEQUENCE: 36
cggcacgagg gggagacctg gaaggaagcg actgcactga tccagaaatg cctcccaggc    60
tatccaggag gggccaagag attaaaagca ggttcagaag gctcagatgc cactcaccag    120

```
acagcagggt cgactgctag tgaccttgag cccagtccgg acagacagac aggcagacag    180
acgcacggac aagcagatgc tccttggcca gctatccact cttctgtgcc tgcttagcgg    240
ggccctgcct acaggctcag ggaggcctga accccagtct cctcgacctc agtcctgggc    300
tgcagccaat cagacctggg ctctgggccc aggggccctg ccccactggt gccagcttc     360
tgcccttggg agctggaagg ccttcttggg cctgcagaaa gccaggcagc tggggatggg    420
caggctgcag cgtgggcaag acgaggtggc tgctgtgact ctgccgctga accctcagga    480
agtgatccag gggatgtgta aggctgtgcc cttcgttcag acgggagt ctcgctatgt      540
tgcccaagct agtcttgagc ttctggcctc aagcaatcct cccacctcag cctcctgagt    600
tctaggtgtt ctcccggccc ggctgctcag ccatacgccc cgaaatcat ctgtgctttg     660
gtcattgctc ctctctctac atccctggct cggaccccac cccactagtc ctgtgcaaca    720
gctgtatgcc tgctcgcaag cgttgggcac cgtggtcct gtggtgtctc actggcagct    780
cagcctcccg tcgacgggtg aagatatcca ccatgctgat cgagggtgt cactgcagcc     840
caaaagcatg aactgagcat ctggatgggt gcacggagac acgcaccttg agaaatgag    900
gggagatgga ccaagaaaga cgtggacctg gatgatgtac tctgggtcaa gagaccaggg    960
atgcagggtt aggcagacag gtccccagag tcctcaccct gctccccaga cagtagacac   1020
agtgcccgtc ctggagttgc accactgata gtcacagcac acaatgattg acaactcact   1080
tttttttttt tttttgagat ggagtctcgc tctgtcgccc aggctggagt gcagtggcgc   1140
aatctcagct cactgcaagc tccacctccc gggtttatgc cattctcctg tctcagcctc   1200
ccgagtagct gggactacag gcacccgcca acacgcccgg staatttttt gtatttttag   1260
taaagacagg gtttcaccgt gttagccagg atggtctcta tctcctgacc tcgtgatctg   1320
cctgccttgg ccttattatt ttttttttaa ggacagagtc tctctctgtc acccaggctg   1380
gagtgcaatg gcgcgatctt ggctcactgt aacttccact tgccaggctc aagcagttct   1440
cctgcctcag cctcctgagt agctgggact acaggcaccc gccaccatgc ccagctaatt   1500
tttgtatttt tagtagagac agagtttcac catattagcc tggctggtct caaactcctg   1560
gcctcaggtg atctgcccac ctcggcctcc caaagtgctg ggatcaaatc cactgttaat   1620
cattaggctg aactgtctct tatagaatga ggtcaaagac actcccagtt gcagggaggg   1680
tagatggccc cacccagacc gagagacaca gtgatgacct cagcctaggg acmccaaaaa   1740
aaaaaaaaaa aaaaaa                                                   1756
```

<210> SEQ ID NO 37
<211> LENGTH: 133
<212> TYPE: PRT
<213> ORGANISM: Artificial Sequence
<220> FEATURE:
<223> OTHER INFORMATION: Homo sapiens
<220> FEATURE:
<221> NAME/KEY: Predicted translation product of SEQ ID NO:36

<400> SEQUENCE: 37

Met Leu Leu Gly Gln Leu Ser Thr Leu Leu Cys Leu Leu Ser Gly Ala
1               5                   10                  15

Leu Pro Thr Gly Ser Gly Arg Pro Glu Pro Gln Ser Pro Arg Pro Gln
            20                  25                  30

Ser Trp Ala Ala Ala Asn Gln Thr Trp Ala Leu Gly Pro Gly Ala Leu
        35                  40                  45

Pro Pro Leu Val Pro Ala Ser Ala Leu Gly Ser Trp Lys Ala Phe Leu

```
              50                  55                  60
Gly Leu Gln Lys Ala Arg Gln Leu Gly Met Gly Arg Leu Gln Arg Gly
 65                  70                  75                  80

Gln Asp Glu Val Ala Ala Val Thr Leu Pro Leu Asn Pro Gln Glu Val
                 85                  90                  95

Ile Gln Gly Met Cys Lys Ala Val Pro Phe Val Gln Thr Arg Glu Ser
            100                 105                 110

Arg Tyr Val Ala Gln Ala Ser Leu Glu Leu Leu Ala Ser Ser Asn Pro
        115                 120                 125

Pro Thr Ser Ala Ser
    130

<210> SEQ ID NO 38
<211> LENGTH: 589
<212> TYPE: DNA
<213> ORGANISM: Homo sapiens
<220> FEATURE:
<221> NAME/KEY: Full-length INSP002 cloned from human heart cDNA

<400> SEQUENCE: 38
gatgctcctt ggccagctat ccactcttct gtgcctgctt agcggggccc tgcctacagg      60
ctcagggagg cctgaacccc agtctcctcg acctcagtcc tgggctgcag ccaatcagac     120
ctgggctctg ggcccagggg ccctgccccc actggtgcca gcttctgccc ttgggagctg     180
gaaggccttc ttgggcctgc agaaagccag gcagctgggg atgggcaggc tgcagcgtgg     240
gcaagacgag gtggctgctg tgactctgcc gctgaaccct caggaagtga tccaggggat     300
gtgtaaggct gtgcccttcg ttcaggtgtt ctcccggccc ggctgctcag ccatacgcct     360
ccgaaatcat ctgtgctttg gtcattgctc ctctctctac atccctggct cggaccccac     420
cccactagtc ctgtgcaaca gctgtatgcc tgctcgcaag cgttgggcac ccgtggtcct     480
gtggtgtctc actggcagct cagcctcccg tcgacgggtg aagatatcca ccatgctgat     540 cgagggtgt cactgcagcc caaaagcatg aactgagcat cgtggatgg               589
```

CYSTINE-KNOT FOLD PROTEIN

REFERENCE TO RELATED APPLICATIONS

This application in a continuation-in-part of International Patent Application PCT/GB02/05865 filed Dec. 20, 2002 and published as WO 03/055911 on Jul. 10, 2003 which claims priority from Great Britain Application No. 0130738.8 filed Dec. 21, 2001. Each of these applications, and each application and patent mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

SUMMARY OF THE INVENTION

This invention relates to a novel protein (INSP002), herein identified as a secreted protein that is a member of the Dan family of the cystine-knot fold cytokine superfamily and to the use of this protein and nucleic acid sequences from the encoding genes in the diagnosis, prevention and treatment of disease.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

Secreted Protein Background

The ability for cells to make and secrete extracellular proteins is central to many biological processes. Enzymes, growth factors, extracellular matrix proteins and signalling molecules are all secreted by cells through fusion of a secretory vesicle with the plasma membrane. In most cases, but not all, proteins are directed to the endoplasmic reticulum and into secretory vesicles by a signal peptide. Signal peptides are cis-acting sequences that affect the transport of polypeptide chains from the cytoplasm to a membrane bound compartment such as a secretory vesicle.

Polypeptides that are targeted to the secretory vesicles are either secreted into the extracellular matrix or are retained in the plasma membrane. The polypeptides that are retained in the plasma membrane will have one or more transmembrane domains. Examples of secreted proteins that play a central role in the functioning of a cell are cytokines, hormones, extracellular matrix proteins (adhesion molecules), proteases, and growth and differentiation factors.

Growth factors represent a relatively large group of polypeptides which share the property of inducing cell multiplication both in vivo and in vitro. Growth factors differ from classical endocrine hormones such as insulin or growth hormone in two important ways. Firstly, endocrine hormones are typically synthesised in specialised glands (such as the pancreas, in the case of insulin) whereas growth factors are often synthesised in multiple types of cells and tissues. Secondly, classical endocrine hormones are released into body fluids at the site of synthesis and are carried to their target tissue in the bloodstream. A hallmark of growth factors is that, in most instances, they act locally within the tissues that they are synthesised in (reviewed in Heath, J K. (1993) Growth Factors, Oxford University Press, Oxford, UK, pp. 15-33).

Although the level of sequence similarity between growth factors is not high, they can be classified into superfamilies based on their structural and functional similarities. Examples of these superfamilies include: (a) the hematopoietic growth factors, such as growth hormone, IL-2, IL-4, G-CSF, and CNTF, which all posses a four-helix-bundle structural motif; (b) the beta-trefoil family members, such as IL-1 beta, IL-1 alpha, FGF, and keratinocyte growth factor; (c) the EGF-like growth factors such as EGF and TGF alpha, which all have a immunoglobulin-like domain; and (d) the cystine-knot growth-factor fold which includes NGF, TGF beta, PDGF, and glycoprotein hormones.

Growth factors are extracellular and in order to exert a biological effect, they interact with specific, high affinity receptors located on the plasma membranes of target cells. The molecular characterisation of a variety of different growth factor receptors has revealed that they fall into defined families: the tyrosine kinase receptors, G-protein associated seven transmembrane receptors, and the serine/threonine kinase receptors. The tyrosine kinase receptors are characterised by an extracellular domain, a transmembrane domain, and an intracellular domain which possess tyrosine kinase activity. The serine/threonine kinase growth factor receptors are similar to the tyrosine kinase receptors with an extracellular domain, a transmembrane domain, and an intracellular domain. The intracellular domain has intrinsic serine/threonine kinase activity.

Deregulation of growth factors is implicated in a variety of disease states, including, but not limited to, oncological diseases (Bartucci M et al, (2001) Cancer Res. September 15; 61 (18):6747-54, Dias S et al., (2001) Proc Natl Acad Sci USA. September 11; 98 (19):10857-62, Djavan B et al., (2001) World J Urol. 19(4):225-33), inflammatory diseases (Fiocchi C. (2001) J Clin Invest. August; 108(4):523-6, Hodge S et al., (2001) Respirology. September; 6 (3):205-211, Fenwick S A et al., (2001) J Anat. September;199 (Pt 3):231-40), neurological diseases (Cooper J D et al., (2001) Proc Natl Acad Sci USA 98(18):10439-44, Fahnestock M et al, (2001) Mol Cell Neurosci 18 (2):210-20), and metabolic diseases (Vickers M H et al., (2001) Endocrinology. 142 (9):3964-73).

Cystine Knot Fold Superfamily

The typical structure seen in the cystine knot superfamily is based on the presence of 6 cysteine residues creating 3 disulphide bonds. Two of the disulphide bonds create a 'ring-like' structure, which is penetrated by the third disulphide bond, (Sun et al. 1995). Cystine knot domains are often found with more than 6 cysteine residues. The extra cysteine residues are normally used to create further disulphide bonds within the cystine knot domain or interchain disulphide bonds, during dimerisation.

This cystine knot superfamily is divided into subfamilies, which include, the glycoprotein hormones (eg. follicle stimulating hormone), the transforming growth factor beta (TGF-Beta) proteins (eg. bone morphogenetic protein 4), the platelet-derived growth factor-like (PDGF-like) proteins (eg. platelet derived growth factor A), nerve growth factors (NGF) (eg. brain-derived neurotrophic factor) and the differential screening-selected gene aberrative in neuroblastoma (DAN) family (eg. cerberus). The DAN subfamily includes Cer1, Cerberus, Caronte, Drm/Gremlin, PRDC, DAN, Dante and CeCan1 (Massague et al. Genes Dev 2000 Mar. 15; 14 (6): 627-44; Massague & Wotton, EMBO J. 2000 Apr. 17;19(8): 1745-54).

It is thought that members of the DAN subfamily may be able to modulate the actions of members of members of the TGFbeta subfamily of proteins (Pearce et al., Dev Biol. 1999 May 1;209(1):98-110). More specifically, it is possible that members of the DAN subfamily are able to modulate the actions of bone morphogenetic proteins (BMPs) during development.

Members of the DAN subfamily have been found to act as antagonists of bone morphogenetic proteins (BMP), which are members of the TGFBeta subfamily of the cystine knot supefamily (Stanley et al., Mech Dev. 1998 October;77(2): 173-84; Massague et al. 2000 (supra); Massague J & Wotton D, 2002 (supra)). BMP monomers homo- or heterodimerise, through the binding of their cystine knot domains, before they interact with cell surface receptors. It is thought that DAN subfamily members are able to bind BMPs through their own cystine knot domains. This prevents the BMP from binding to its natural dimerisation partner and as a result, the BMP is no longer able to interact with its cell surface signaling receptor. Experiments specifically looking at DAN, Cer1, and DRM, have shown that they inhibit the action of BMP4 (Pearce et al. 1999, (supra)).

A greater understanding of the function of cerberus has been achieved as a result of binding studies (Piccolo S. et al., Nature. 1999 Feb. 25;397(6721):707-10). The first functional studies carried out on cerberus used the *Xenopus laevis* cerberus protein (cer). Microinjection of *Xeonpus* cerberus mRNA in *Xenopus* embryos revealed that the cer protein induced formation of ectopic heads in the anterior endoderm of the Spemann's organizer (Bouwmeester et al. Nature 1996 Aug. 15;382(6592):595-601; Bouwmeester T., Int J Dev Biol. 200, 145(1 Spec No):251-8). Binding studies carried out by Piccolo and co-workers revealed that the *Xenopus* cerberus protein binds and inhibit the actions of Nodal, BMP and Wnt proteins via independent sites. More specifically, they found that cerberus has a high specific affinity for and inhibitory effect on Xnr-1 (Nodal family member), BMP4 (BMP family member) and Xwmt-8 (Wnt family member). This work links cerberus, and hence other members of the DAN family, to developmental and tissue differentiation pathways.

Sclerostin, encoded by the gene SOST, is also a member of the DAN subfamily (Brumkow et al, 2001, Am. J. Hum. Genet. 68:577-589). SOST has been linked to sclerosteosis, an autosomal recessive sclerosing bone dysplasia. The phenotype associated by sclerosteosis is progressive skeletal overgrowth, which can lead to gigantism, distortion of the facies and entrapment of the seventh and eighth cranial nerves (Brumkow et al. 2001, (supra)). The link between sclerosteosis and SOST was determined through homozygosity mapping in families who are affected by the disease. Brumkow and co-workers identified a similarity between the phenotype associated with sclerosteosis and effects associated with other DAN subfamily members. This link was strengthened by the suggestion that sclerosteosis may arise due to lose of a negative regulator of TGFbeta subfamily member, more specially a BMP.

Identification of secreted proteins and in particular growth factors, such as members of the cystine knot fold superfamily, and in particular members of the DAN subfamily, is therefore of extreme importance in increasing understanding of the underlying pathways that lead to the disease states and associated disease states, mentioned above, and in developing more effective gene or drug therapies to treat these disorders.

THE INVENTION

The invention is based on the discovery that the INSP002 protein functions as a secreted protein and moreover as a secreted protein of the DAN subfamily of the cystine knot fold cytokine superfamily.

In a first aspect, the invention provides a polypeptide which:

(i) comprises the amino acid sequence as recited in SEQ ID NO:2, SEQ ID NO:4, or SEQ ID NO: 7, (ii) is a fragment thereof having the function of a secreted protein, preferably the function of a member of the cystine knot fold cytokine superfamily, preferably a member of the DAN subfamily, or having an antigenic determinant in common with the polypeptides of (i); or (iii) is a functional equivalent of (i) or (ii).

Preferably, the polypeptide according to this first aspect of the invention:

(i) comprises the amino acid sequence as recited in SEQ ID NO:6 or SEQ ID NO:8, (ii) is a fragment thereof having the function of a secreted protein, preferably the function of a member of the cystine knot fold cytokine superfamily, preferably a member of the DAN subfamily, or having an antigenic determinant in common with the polypeptides of (i); or (iii) is a functional equivalent of (i) or (ii).

According to a further embodiment of this first aspect of the invention, there is provided a polypeptide which:

(i) consists of the amino acid sequence as recited in SEQ ID NO:2, SEQ ID NO:4, SEQ ID NO:6, SEQ ID NO:7, or SEQ ID NO:8,
(ii) is a fragment thereof having the function of a secreted protein, preferably the function of a member of the cystine knot fold cytokine superfamily, preferably a member of the DAN subfamily, or having an antigenic determinant in common with the polypeptides of (i); or
(iii) is a functional equivalent of (i) or (ii).

The polypeptide having the sequence recited in SEQ ID NO:2 is referred to hereafter as "the INSP002 exon 1 polypeptide". The polypeptide having the sequence recited in SEQ ID NO:4 is referred to hereafter as "the INSP002 exon 2 polypeptide". The polypeptide having the sequence recited in SEQ ID NO:6 is referred to hereafter as "the INSP002 polypeptide". The first 22 amino acids of the INSP002 exon 1 polypeptide are a signal peptide and the INSP002 polypeptide sequences without the signal sequence are recited in SEQ ID NO: 7 and SEQ ID NO:8. The polypeptide having the sequence recited in SEQ ID NO:7 is referred to hereafter as "the INSP002 exon 1 polypeptide without signal peptide". The polypeptide having the sequence recited in SEQ ID NO:8 is referred to hereafter as "the INSP002 polypeptide without signal peptide".

According to a further embodiment of this first aspect of the invention, there is provided a polypeptide which:
(i) comprises or consists of the amino acid sequence as recited in SEQ ID NO:14,
(ii) is a fragment thereof having the function of a secreted protein, preferably the function of a member of the cystine knot fold cytokine superfamily, preferably a member of the DAN subfamily, or having an antigenic determinant in common with the polypeptide of (i), or
(iii) is a functional equivalent of (i) or (ii).

The polypeptide having the sequence recited in SEQ ID NO:14 is a variant of the INSP002 polypeptide. It is identical to the INSP002 polypeptide except that it contains a two amino acid deletion at positions 107 and 108 and a single amino acid substitution at position 110 compared to the INSP002 polypeptide. The polypeptide having the sequence recited in SEQ ID NO:14 is referred to hereafter as "the variant INSP002 polypeptide".

Preferably, a polypeptide according to the first aspect of the invention functions as a member of the cystine knot fold cytokine superfamily, preferably as a member of the DAN subfamily. The term "cystine knot fold cytokine" is well understood in the art and the skilled worker will readily be able to ascertain whether a polypeptide functions as a member of the cystine knot fold cytokine superfamily using one of a variety of assays known in the art.

In particular, the skilled person may be able to ascertain whether a polypeptide functions as a member of the DAN subfamily by assaying whether it is an antagonist of TGFBeta superfamily members and in particular, whether it is a BMP antagonist. The *Xenopus* embryo may be used as a system for assaying whether a polypeptide functions as a BMP antagonist since several BMPs are expressed in the *Xenopus* embryo (Chang C. et al. 1999, Development 126:3347-3357, Hawley S. et al., 1995, Genes Dev. 9:2923-2935, Hemmati-Brivanlou, A., and G. H. Thomsen. 1995, Dev. Genet. 17:78-89, Jones C. M. et al., 1992, Development 115:639-647). Overexpression of BMP-2/4-class or BMP-7-class signals in the early mesoderm induces ventral fates, while inhibitors of these signals (such as Noggin, Xnr3, Chordin, or Follistatin) induce dorsal fates. The effect of a polypeptide on embryonic development can therefore be used to determine whether that polypeptide is a BMP antagonist.

The term "INSP002 polypeptides" as used herein includes polypeptides comprising the INSP002 exon 1 polypeptide, the INSP002 exon 1 polypeptide without signal peptide, the INSP002 exon 2 polypeptide, the INSP002 polypeptide or the INSP002 polypeptide without signal peptide, as well as polypeptides consisting of the INSP002 exon 1 polypeptide, the INSP002 exon 1 polypeptide without signal peptide, the INSP002 exon 2 polypeptide, the INSP002 polypeptide, the INSP002 polypeptide without signal peptide or the variant INSP002 polypeptide.

In a second aspect, the invention provides a purified nucleic acid molecule which encodes a polypeptide of the first aspect of the invention.

Preferably, the purified nucleic acid molecule comprises the nucleic acid sequence as recited in SEQ ID NO:1 (encoding the INSP002 exon 1 polypeptide), SEQ ID NO:3 (encoding the INSP002 exon 2 polypeptide), SEQ ID NO:5 (encoding the INSP002 polypeptide), or SEQ ID NO:13 (encoding the variant INSP002 polypeptide) or is a redundant equivalent or fragment of either of these sequences.

The invention further provides that the purified nucleic acid molecule consists of the nucleic acid sequence as recited in SEQ ID NO:1 (encoding the INSP002 exon 1 polypeptide), SEQ ID NO:3 (encoding the INSP002 exon 2 polypeptide), SEQ ID NO:5 (encoding the INSP002 polypeptide) or SEQ ID NO:13 (encoding the variant INSP002 polypeptide) or is a redundant equivalent or fragment of either of these sequences.

According to one embodiment of this aspect of the invention, the purified nucleic acid molecule does not contain the 5' untranslated region located upstream of the nucleic acid sequence encoding the INSP002 exon 1 polypeptide and the nucleic acid sequence encoding the INSP002 polypeptide (nucleotides 1 to 151 of SEQ ID NO:1 and SEQ ID NO:5). According to this embodiment, the purified nucleic acid molecule preferably comprises nucleotides 152 to 475 of SEQ ID NO:1 or nucleotides 152 to 721 of SEQ ID NO:5. The invention further provides a purified nucleic acid molecule consisting of nucleotides 152 to 475 of SEQ ID NO:1 or nucleotides 152 to 721 of SEQ ID NO:5. The nucleotide sequence coding for the INSP002 polypeptide without the 5' untranslated region (nucleotides 152 to 721 of SEQ ID NO:5) is given in SEQ ID NO:11 and the nucleotide sequence coding for the INSP002 exon 1 polypeptide (nucleotides 152 to 475 of SEQ ID NO:1) without the 5' untranslated region is given in SEQ ID NO:12.

According to a further embodiment of this aspect, the purified nucleic acid molecule does not encode the signal peptide located at the start of the INSP002 exon 1 polypeptide and the INSP002 polypeptide (nucleotides 152 to 217 of SEQ ID NO:1 and SEQ ID NO:5). According to this embodiment, the purified nucleic acid molecule preferably comprises nucleotides 218 to 475 of SEQ ID NO:1 (encoding the INSP002 exon 1 polypeptide without signal peptide) or nucleotides 218 to 721 of SEQ ID NO:5 (encoding the INSP002 polypeptide without signal peptide). The invention further provides a purified nucleic acid molecule consisting of nucleotides 218 to 475 of SEQ ID NO:1 (encoding the INSP002 exon 1 polypeptide without signal peptide) or nucleotides 218 to 721 of SEQ ID NO:5 (encoding the INSP002 polypeptide without signal peptide). The nucleotide sequence encoding the mature INSP002 polypeptide (SEQ ID NO:7) is given in SEQ ID NO:9 and the nucleotide sequence encoding the mature INSP002 exon 1 polypeptide is given in SEQ ID NO:10.

According to a further embodiment of this aspect of the invention, the purified nucleic acid molecule does not contain the 5' untranslated region located upstream of the nucleic acid sequence encoding the variant INSP002 polypeptide (nucleotides 1 to 68 of SEQ ID NO:13). According to this embodiment, the purified nucleic acid molecule preferably comprises or consists of nucleotides 69 to 719 of SEQ ID NO:13. The nucleotide sequence coding for the variant INSP002 polypeptide without the 5'untranslated region (nucleotides 69 to 719 of SEQ ID NO:13) is given in SEQ ID NO:15.

In a third aspect, the invention provides a purified nucleic acid molecule which hydridizes under high stringency conditions with a nucleic acid molecule of the second aspect of the invention.

In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand which binds specifically to, and which preferably inhibits the cystine knot fold cytokine activity of a polypeptide of the first aspect of the invention. Preferably, the ligand inhibits the function of a polypeptide of the first aspect of the invention which is a member of the DAN subfamily of cystine knot fold cytokines. Ligands to a polypeptide according to the invention may come in various forms, including natural or modified substrates, enzymes, receptors, small organic molecules such as small natural or synthetic organic molecules of up to 2000 Da, preferably 800 Da or less, peptidomimetics, inorganic molecules, peptides, polypeptides, antibodies, structural or functional mimetics of the aforementioned. In a seventh aspect, the invention provides a compound that is effective to alter the expression of a natural gene which encodes a polypeptide of the first aspect of the invention or to regulate the activity of a polypeptide of the first aspect of the invention.

A compound of the seventh aspect of the invention may either increase (agonise) or decrease (antagonise) the level of expression of the gene or the activity of the polypeptide. Importantly, the identification of the function of the INSP002 polypeptides allows for the design of screening methods capable of identifying compounds that are effective in the treatment and/or diagnosis of disease.

In an eighth aspect, the invention provides a polypeptide of the first aspect of the invention, or a nucleic acid molecule of the second or third aspect of the invention, or a vector of the fourth aspect of the invention, or a ligand of the fifth aspect of the invention, or a compound of the sixth aspect of the invention, for use in therapy or diagnosis. These molecules may also be used in the manufacture of a medicament for the treatment of cell proliferative disorders, autoimmune/inflammatory disorders, cardiovascular disorders, neurological disorders, developmental disorders, metabolic disorders, infections and other pathological conditions.

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro. Similar methods may be used for monitoring the therapeutic treatment of disease in a patient, wherein altering the level of expression or activity of a polypeptide or nucleic acid molecule over the period of time towards a control level is indicative of regression of disease.

The disorder or disease in the ninth and tenth aspects of the invention is preferably one in which aberrant levels of a cystine knot fold cytokine, preferably a member of the DAN subfamily, are implicated. The disease or disorder may also be one in which aberrant levels of a ligand of a cystine knot fold cytokine, preferably a member of the DAN subfamily, are implicated. For example, the disease or disorder may be one in which aberrant levels of a TGFBeta superfamily member are implicated. In particular, the disease or disorder may be one in which BMPs are implicated, such as neuropathies, nephropathies such as diabetic mephropathy, cancer, wound healing, fibrosis, osteopenia, osteoporosis, fractures and sclerosteosis.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different such methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

In a tenth aspect, the invention provides for the use of a polypeptide of the first aspect of the invention as a secreted protein. Preferably, the invention provides for the use of a polypeptide of the first aspect of the invention as a cytokine, more preferably as a cystine knot fold cytokine and in particular as a member of the DAN subfamily of cystine knot fold cytokines.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in the manufacture of a medicament for the diagnosis or treatment of a disease.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a ligand of the sixth aspect of the invention, or a compound of the seventh aspect of the invention.

The disease in the twelfth and thirteenth aspects of the invention is preferably a disease in which aberrant levels of a cystine knot fold cytokine, preferably of a member of the DAN subfamily, are implicated. The disease may also be one in which aberrant levels of a ligand of a cystine knot fold cytokine, preferably a ligand of a member of the DAN subfamily, are implicated. For example, the disease may be a disease in which aberrant levels of a TGFBeta superfamily member are implicated. In particular, the disease or disorder may be one in which BMPs are implicated, such as neuropathies, nephropathies such as diabetic mephropathy, cancer, wound healing, fibrosis, osteopenia, osteoporosis, fractures and sclerosteosis.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, ligand or compound administered to the patient should be an antagonist. Examples of such antagonists include antisense nucleic acid molecules, ribozymes and ligands, such as antibodies.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of the those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or preproprotein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

The functionally-equivalent polypeptides of the first aspect of the invention may be polypeptides that are homologous to the INSP002 polypeptides. Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A.M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Homologous polypeptides therefore include natural biological variants (for example, allelic variants or geographical variations within the species from which the polypeptides are derived) and mutants (such as mutants containing amino acid substitutions, insertions or deletions) of the INSP002 polypeptides. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

Typically, greater than 30% identity between two polypeptides is considered to be an indication of functional equivalence. Preferably, functionally equivalent polypeptides of the first aspect of the invention have a degree of sequence identity with the INSP002 polypeptide, or with active fragments thereof, of greater than 35%. More preferred polypeptides have degrees of identity of greater than 35%, 40%, 50%, 60%, 70%, 80%, 90%, 95%, 98%, 99% or more, respectively.

Sequence identity with respect to any of the sequences presented here can be determined by a simple "eyeball" comparison (i.e. a strict comparison) of any one or more of the sequences with another sequence to see if that other sequence has, for example, at least 70% sequence identity to the sequence(s).

Alternatively, relative sequence identity can also be determined by commercially available computer programs that can calculate % identity between two or more sequences using any suitable algorithm for determining identity, using for example default parameters. A typical example of such a computer program is CLUSTAL. Other computer program methods to determine identify and similarity between the two sequences include but are not limited to the GCG program package (Devereux et al 1984 Nucleic Acids Research 12: 387) and FASTA (Atschul et al 1990 J Molec Biol 403-410).

The sequence identity or percent homology for proteins and nucleic acids can also be calculated as (Nref−Ndif)×100/Nref, wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (Ndif=2 and Nref=8).

Percent homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S. A.; Devereux et al., 1984, Nucleic Acids Research 12:387). Examples of other software than can perform sequence comparisons include, but are not limited to, the BLAST package (Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (Ausubel et al., 1999 ibid, pages 7-58 to 7-60).

The functionally-equivalent polypeptides of the first aspect of the invention may also be polypeptides which have been identified using one or more techniques of structural alignment. For example, the Inpharmatica Genome Threader technology that forms one aspect of the search tools used to generate the Biopendium search database may be used (see co-pending United Kingdom patent application PCT/GB01/01105) to identify polypeptides of presently-unknown function which, while having low sequence identity as compared to the INSP002 polypeptides, are predicted to have secreted molecule activity, by virtue of sharing significant structural homology with the INSP002 polypeptide sequences. By "significant structural homology" is meant that the Inpharmatica Genome Threader predicts two proteins to share structural homology with a certainty of 10% and above.

The polypeptides of the first aspect of the invention also include fragments of the INSP002 polypeptides and fragments of the functional equivalents of the INSP002 polypeptides, provided that those fragments retain cystine knot fold cytokine activity, preferably the activity of a member of the DAN cystine knot fold subfamily or have an antigenic determinant in common with the INSP002 polypeptides.

As used herein, the term "fragment" refers to a polypeptide having an amino acid sequence that is the same as part, but not all, of the amino acid sequence of the INSP002 polypeptides or one of its functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known secreted proteins.

Preferably, the affinity is at least 1.5-fold, 2-fold, 5-fold 10-fold, 100-fold, $10^3$-fold, $10^4$-fold, $10^5$-fold or $10^6$-fold greater for a polypeptide of the invention than for known secreted proteins such as cystine knot fold cytokines and in particular such as members of the DAN subfamily.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988); Kabat et al., J. Immunol., 147, 1709 (1991); Queen et al., Proc. Natl. Acad. Sci. USA, 86, 10029 (1989); Gorman et al., Proc. Natl. Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode the polypeptide sequences recited in SEQ ID NO:2, SEQ ID NO:4, SEQ ID NO:7, SEQ ID NO:6, SEQ ID NO:8 and SEQ ID NO:14 and functionally equivalent polypeptides. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

A nucleic acid molecule which encodes the polypeptide of SEQ ID NO:2 may be identical to the coding sequence of the nucleic acid molecule shown in SEQ ID NO:1 (nucleotides 152 to 475), as recited in SEQ ID NO:12. A nucleic acid molecule which encodes the polypeptide of SEQ ID NO:7 may be identical to the coding sequence of the nucleic acid molecule shown in SEQ ID NO:1 (nucleotides 218 to 475), as recited in SEQ ID NO:10. A nucleic acid molecule which encodes the polypeptide of SEQ ID NO:4 may be identical to the coding sequence of the nucleic acid molecule shown in SEQ ID NO:3. A nucleic acid molecule which encodes the polypeptide of SEQ ID NO: 6 may be identical to the coding sequence of the nucleic acid molecule shown in SEQ ID NO:5 (nucleotides 152 to 721), as recited in SEQ ID NO:11. A nucleic acid molecule which encodes the polypeptide of SEQ ID NO: 8 may be identical to the coding sequence of the nucleic acid molecule shown in SEQ ID NO:5 (nucleotides 218 to 721), as recited in SEQ ID NO:9. A nucleic acid molecule which encodes the polypeptide of SEQ ID NO:14 may be identical to the coding sequence of the nucleic acid molecule shown in SEQ ID NO:13 (nucleotides 69 to 719), as recited in SEQ ID NO:15.

These molecules also may have a different sequence which, as a result of the degeneracy of the genetic code, encodes a polypeptide of SEQ ID NO:2, SEQ ID NO:4, SEQ ID NO: 7, SEQ ID NO:6, SEQ ID NO: 8 or SEQ ID NO:14. Such nucleic acid molecules that encode the polypeptide of SEQ ID NO:2, SEQ ID NO:4, SEQ ID NO:7, SEQ ID NO:6, SEQ ID NO:8 or SEQ ID NO:14 may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used here refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5× SSC (150 mM NaCl, 15 mM trisodium citrate), 50 mM sodium phosphate (pH7.6), 5× Denhardts solution, 10% dextran sulphate, and 20 microgram/ml denatured, sheared salmon sperm DNA, followed by washing the filters in 0.1× SSC at approximately 65° C. Low stringency conditions involve the hybridisation reaction being carried out at 35° C. (see Sambrook et al. [supra]). Preferably, the conditions used for hybridization are those of high stringency.

Preferred embodiments of this aspect of the invention are nucleic acid molecules that are at least 70% identical over their entire length to a nucleic acid molecule encoding the INSP002 polypeptides (SEQ ID NO:2, SEQ ID NO:4, SEQ ID NO:7, SEQ ID NO:6, SEQ ID NO:8 and SEQ ID NO:14) and nucleic acid molecules that are substantially complementary to such nucleic acid molecules. Preferably, a nucleic acid molecule according to this aspect of the invention comprises a region that is at least 80% identical over its entire length to: the coding sequences for SEQ ID NO:2 and SEQ ID NO:7 given in SEQ ID NO:1, SEQ ID NO:10 and SEQ ID NO:12; the coding sequence for SEQ ID NO:4 given in SEQ ID NO:3; the coding sequences for SEQ ID NO:6 and SEQ ID NO:8 given in SEQ ID NO:5, SEQ ID NO:9 and SEQ ID NO:11; or the coding sequences for SEQ ID NO:14 given in SEQ ID NO:13 and SEQ ID NO:15; or is a nucleic acid molecule that is complementary thereto. In this regard, nucleic acid molecules at least 90%, preferably at least 95%, more preferably at least 98% or 99% identical over their entire length to the same are particularly preferred. Preferred embodiments in this respect are nucleic acid molecules that encode polypeptides which retain substantially the same biological function or activity as the INSP002 polypeptides.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP002 polypeptides and to isolate cDNA and genomic clones of homologous or orthologous genes that have a high sequence similarity to the gene encoding this polypeptide.

In this regard, the following techniques, among others known in the art, may be utilised and are discussed below for purposes of illustration. Methods for DNA sequencing and analysis are well known and are generally available in the art and may, indeed, be used to practice many of the embodiments of the invention discussed herein. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer).

One method for isolating a nucleic acid molecule encoding a polypeptide with an equivalent function to that of the INSP002 polypeptides is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989, 1992). Probes comprising at least 15, preferably at least 30, and more preferably at least 50, contiguous bases that correspond to, or are complementary to, nucleic acid sequences from the appropriate encoding gene (SEQ ID NO:1, SEQ ID NO:3, SEQ ID NO:5, SEQ ID NO:9, SEQ ID NO:10, SEQ ID NO:11, SEQ ID NO:12, SEQ ID NO:13 or SEQ ID NO:15), are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic., 1, 111-

119). Another method which may be used to retrieve unknown sequences is that of Parker, J. D. et al. (1991); Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, S M et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., [supra]. Particularly suitable methods include calcium phosphate transfection, DEAE-dextran mediated transfection, transvection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines.

In the baculovirus system, the materials for baculovirus/insect cell expression systems are commercially available in kit form from, inter alia, Invitrogen, San Diego Calif. (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as Drosophila S2 and Spodoptera Sf9 cells.

There are many plant cell culture and whole plant genetic expression systems known in the art. Examples of suitable plant cellular genetic expression systems include those described in U.S. Pat. Nos. 5,693,506; 5,659,122; and 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include streptococci, staphylococci, *E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk- or aprt± cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al. (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide. Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D. J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1 (2):Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

A preferred method for identifying an agonist or antagonist compound of a polypeptide of the present invention comprises:

(a) contacting a cell expressing on the surface thereof the polypeptide according to the first aspect of the invention, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by measuring the level of a signal generated from the interaction of the compound with the polypeptide.

A further preferred method for identifying an agonist or antagonist of a polypeptide of the invention comprises:

(a) contacting a cell expressing on the surface thereof the polypeptide, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by comparing the level of a signal generated from the interaction of the compound with the polypeptide with the level of a signal in the absence of the compound.

In further preferred embodiments, the general methods that are described above may further comprise conducting the identification of agonist or antagonist in the presence of labelled or unlabelled ligand for the polypeptide.

In another embodiment of the method for identifying agonist or antagonist of a polypeptide of the present invention comprises:

determining the inhibition of binding of a ligand to cells which have a polypeptide of the invention on the surface thereof, or to cell membranes containing such a polypeptide, in the presence of a candidate compound under conditions to permit binding to the polypeptide, and determining the amount of ligand bound to the polypeptide. A compound capable of causing reduction of binding of a ligand is considered to be an agonist or antagonist. Preferably the ligand is labelled.

More particularly, a method of screening for a polypeptide antagonist or agonist compound comprises the steps of:

(a) incubating a labelled ligand with a whole cell expressing a polypeptide according to the invention on the cell surface, or a cell membrane containing a polypeptide of the invention, (b) measuring the amount of labelled ligand bound to the whole cell or the cell membrane;

(c) adding a candidate compound to a mixture of labelled ligand and the whole cell or the cell membrane of step (a) and allowing the mixture to attain equilibrium;

(d) measuring the amount of labelled ligand bound to the whole cell or the cell membrane after step (c); and (e) comparing the difference in the labelled ligand bound in step (b) and (d), such that the compound which causes the reduction in binding in step (d) is considered to be an agonist or antagonist.

The polypeptides may be found to modulate a variety of physiological and pathological processes in a dose-dependent manner in the above-described assays. Thus, the "functional equivalents" of the polypeptides of the invention include polypeptides that exhibit any of the same modulatory activities in the above-described assays in a dose-dependent manner. Although the degree of dose-dependent activity need not be identical to that of the polypeptides of the invention, preferably the "functional equivalents" will exhibit substantially similar dose-dependence in a given activity assay compared to the polypeptides of the invention. In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the polypeptide from suitably manipulated cells or tissues. The formation of binding complexes between the polypeptide and the compound being tested may then be measured.

Assay methods that are also included within the terms of the present invention are those that involve the use of the genes and polypeptides of the invention in overexpression or ablation assays. Such assays involve the manipulation of levels of these genes/polypeptides in cells and assessment of the impact of this manipulation event on the physiology of the manipulated cells. For example, such experiments reveal details of signaling and metabolic pathways in which the particular genes/polypeptides are implicated, generate information regarding the identities of polypeptides with which the studied polypeptides interact and provide clues as to methods by which related genes and proteins are regulated.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.).

The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6 (4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent. Where the aforementioned polypeptide or nucleic acid molecule is one that is up-regulated, vaccine development can involve the raising of antibodies or T cells against such agents (as described in WO00/29428).

Vaccines according to the invention may either be prophylactic (ie. to prevent infection) or therapeutic (ie. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607.

The technology referred to as jet injection (see, for example, www.powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;
b) contacting a control sample with said probe under the same conditions used in step a);
c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:

a) obtaining a tissue sample from a patient being tested for disease;
b) isolating a nucleic acid molecule according to the invention from said tissue sample; and
c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mis-matched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230: 1242). Sequence changes at specific locations may also be revealed by nuclease protection assays, such as RNase and S1 protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. 14: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application WO95/251116 (Baldeschweiler et al). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation. The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:
(a) a nucleic acid molecule of the present invention;
(b) a polypeptide of the present invention; or
(c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease, particularly cell proliferative disorders, autoimmune/inflammatory disorders, cardiovascular disorders, neurological disorders, developmental disorders, metabolic disorders, infections and other pathological conditions. The disease or disorder is preferably a disease in which aberrant levels of a cystine knot fold cytokine, preferably of a member of the DAN subfamily, are implicated. The disease or disorder may also be one in which aberrant levels of a ligand of a cystine knot fold cytokine, preferably a ligand of a member of the DAN subfamily, are implicated. For example, the disease or disorder may be one in which aberrant levels of a TGFBeta superfamily member are implicated. In particular, the disease or disorder may be one in which BMPs are implicated, such as neuropathies, nephropathies such as diabetic mephropathy, cancer, wound healing, fibrosis, osteopenia, osteoporosis, fractures and sclerosteosis. Various aspects and embodiments of the present invention will now be described in more detail by way of example, with particular reference to INSP002 polypeptides.

It will be appreciated that modification of detail may be made without departing from the scope of the invention.

BRIEF DESCRIPTION OF THE FIGURES

FIG. 1: Results from BLAST against NCBI non-redundant database using combined SEQ ID NO:2 and SEQ ID NO:4 polypeptide sequence.

FIG. 2 Alignment generated by BLAST between combined SEQ ID NO:2 and SEQ ID NO:4 polypeptide sequence and the closet related sequence, *Homo sapiens* cerberus-related 1 protein.

FIG. 3: Top four NCBI-nr and NCBI-nt database BLAST hits against INSP002 on 26 Nov. 2002

FIG. 4: Alignment of INSP002 with AK095926.1

FIG. 5: Alignment of INSP002 with IMAGE: 4558384

FIG. 6: INSP002 nucleotide sequence with translation

FIG. 7: INSP002 partial cloned sequence with translation

FIG. 8: Map of PCRII-TOPO-INSP002 partial

FIG. 9: Alignment of INSP002 prediction (top) and partial cloned sequence (bottom)

FIG. 10: Nucleotide sequence and translation of cDNA insert in Image:4558384

FIG. 11: Alignment of sequences of INSP002 prediction (top) with IMAGE: 4558384 (BC025333.1) (bottom)

FIG. 12: Nucleotide sequence and translation of INSP002V generated by PCR from Image 4558384

FIG. 13: Map of pCR4blunt-TOPO-INSP002V

FIG. 14: Comparison between INSP002 Prediction (top) and INSP002V Variant sequence (bottom)

FIG. 15: Map of expression vector pEAK12d

FIG. 16: Map of Gateway vector pDONR201

FIG. 17: Map of pEAK12d-INSP002-V-6HIS

FIG. 18: Sequence of full-length INSP002 cloned from heart.

FIG. 19: May of plasmid pCR4-blunt TOPO-INSP002FL encoding full-length INSP002 cloned from heart is shown in FIG. 19.

EXAMPLES

Example 1

Comparison of INSP002 Protein with Proteins in Sequence Database

The polypeptide sequence derived from combining SEQ ID NO:2 and SEQ ID NO:4, which represents the translation of consecutive exons from INSP002 was used as a BLAST query against the NCBI non-redundant Sequence database.

The top ten matches include sequences annotated as cerberus or cerberus related proteins, which are members of the cystine knot family, all of which align to the query sequence with highly significant E-values ($2E^{-10}$ to $3E^{-06}$) (FIG. 1). FIG. 2 shows the alignment of the INSP002 query sequence to the sequence of *Homo sapiens* cerberus-related 1 protein (Feng et al. 2001).

The polypeptide sequence derived from combining SEQ ID NO:2 and SEQ ID NO:4, which represents the translation of consecutive exons from INSP002 was inputted into SignalP V2.0.b2 (Nielsen et al. 1997 Protein Eng 1:1-6). The program predicted that the polypeptide sequence had a signal peptide. The most likely cleavage site for the signal peptide is to be found between residues 22 and 23 of the polypeptide sequence, INSP002, derived from combining SEQ ID NO:2 and SEQ ID NO:4.

The nucleotide sequence SEQ ID NO:1, encoding the polypeptide SEQ ID NO:2 exon 1, comprises of 5' untranslated region (5'UTR) and protein coding sequence (CDS). The CDS starts at nucleotide 152.

Example 2

Repetition of BLAST Searches

BLAST searches of the NCBI-nr and NCBI-nt databases were conducted on 26 Nov. 2002 using the polypeptide sequence of SEQ ID NO:6, derived from combining SEQ ID NO:2 and SEQ ID NO:4. The top four hits identified by these searches are shown in FIG. 3.

The searches revealed that the INSP002 polypeptide is identical to hypothetical protein FLJ38607 at the amino acid level and the corresponding nucleotide sequence AK095926, cloned from the heart and deposited on 16 Jul. 2002. FIG. 4 shows the alignment of the INSP002 query sequence with the protein derived from the AK095926 cDNA clone.

The exon 1 and exon 2 splice junction predicted for INSP002 is proven experimentally by the existence of AK095926.

(Stratagene). Bacteriophage λ DNA was prepared from small scale cultures of infected *E. coli* host strain using the Wizard Lambda Preps DNA purification system according to the manufacturer's instructions (Promega, Corporation, Madison Wis.) The list of libraries and host strains used is shown in Table I.

ii) PCR of Virtual cDNAs from Phage Library DNA

A partial cDNA encoding INSP002 (FIG. 6) was obtained as a PCR amplification product of 159 bp (FIG. 7) using gene specific cloning primers (INSP002-CP1 and INSP002-CP2, FIG. 6 and Table II). The PCR was performed in a final volume of 50 μl containing 1×AmpliTaq™ buffer, 200 μM dNTPs, 50 pmoles each of cloning primers, 2.5 units of AmpliTaq™ (Perkin Elmer) and 100 ng of each phage library DNA using an MJ Research DNA Engine, programmed as follows: 94° C., 1 min; 40 cycles of 94° C., 1 min, x° C., and y min and 72° C., (where x is the lowest Tm −5° C. and y=1 min per kb of product); followed by 1 cycle at 72° C. for 7 min and a holding cycle at 4° C.

The amplification products were visualized on 0.8% agarose gels in 1× TAE buffer Invitrogen) and PCR products migrating at the predicted molecular mass were purified from the gel using the Wizard PCR Preps DNA Purification System (Promega). PCR products eluted in 50 μl of sterile water were either subcloned directly or stored at −20° C.

iii) Gene Specific Cloning Primers for PCR

Pairs of PCR primers having a length of between 18 and 25 bases were designed for amplifying the full length sequence of the virtual cDNA using Primer Designer Software (Scientific & Educational Software, PO Box 72045, Durham, N.C. 27722-2045, USA). PCR primers were optimized to have a Tm close to 55±10° C. and a GC content of 40-60%.

Primers were selected which had high selectivity for the target sequence INSP002 (little or no specific priming to other templates).

iv) Subcloning of PCR Products

PCR products were subcloned into the topoisomerase I modified cloning vector (pCR II TOPO) using the TOPO TA

```
    450          .    :    .    :    .    :    .    :
    451 GATGTGTAAGGCTGTGCCCTTCGTTCAG         GTGTTCTCCCGGC
        |||||||||||||||||||||||||||||>>>...>>>|||||||||||||
  10225 GATGTGTAAGGCTGTGCCCTTCGTTCAGGTG...CAGGTGTTCTCCCGGC
        Exon1                                 Exon2

500          .    :    .    :    .    :    .    :
    492 CCGGCTGCTCAGCCATACGCCTCCGAAATCATCTGTGCTTTGGTCATTGC
        ||||||||||||||||||||||||||||||||||||||||||||||||||
  13670 CCGGCTGCTCAGCCATACGCCTCCGAAATCATCTGTGCTTTGGTCATTGC
```

The searches also revealed that parts of the INSP002 are identical to IMAGE clone 4558384 (BC025333.1) deposited on 8 Mar. 2002. FIG. 5 shows the alignment of parts of the INSP002 query sequence with IMAGE clone 4558384.

Example 3

Partial Cloning of cDNA for INSP002 i) cDNA Libraries

Human cDNA libraries (in bacteriophage lambda (λ) vectors) were purchased from Stratagene or Clontech or prepared at the Serono Pharmaceutical Research Institute in λ ZAP or λ GT10 vectors according to the manufacturer's protocol cloning kit purchased from the Invitrogen Corporation (cat. No. K4600-01 and K4575-01 respectively) using the conditions specified by the manufacturer. Briefly, 4 μl of gel purified PCR product from the human fetal kidney library (library number 12) amplification was incubated for 15 min at room temperature with 1 μl of TOPO vector and 1 μl salt solution. The reaction mixture was then transformed into *E. coli* strain TOP10 (Invitrogen) as follows: a 50 μl aliquot of One Shot TOP10 cells was thawed on ice and 2 μl of TOPO reaction was added. The mixture was incubated for 15 min on ice and then heat shocked by incubation at 42° C. for exactly 30 s. Samples were returned to ice and 250 μl of warm SOC media (room temperature) was added. Samples were incubated with shaking (220 rpm) for 1 h at 37° C. The transformation mixture was then plated on L-broth (LB) plates containing ampicillin (100 μg/ml) and incubated overnight at 37° C. Ampicillin resistant colonies containing cDNA inserts were identified by colony PCR.

v) Colony PCR

Colonies were inoculated into 50 μl sterile water using a sterile toothpick. A 10 μl aliquot of the inoculum was then subjected to PCR in a total reaction volume of 20 μl as described above, except the primers pairs used were SP6 and T7. The cycling conditions were as follows: 94° C., 2 min; 30 cycles of 94° C., 30 sec, 47° C., 30 sec and 72° C. for 1 min); 1 cycle, 72° C., 7 min. Samples were then maintained at 4° C. (holding cycle) before further analysis.

PCR reaction products were analyzed on 1% agarose gels in 1× TAE buffer. Colonies which gave the expected PCR product size (159 bp cDNA+187 bp due to the multiple cloning site or MCS) were grown up overnight at 37° C. in 5 ml L-Broth (LB) containing ampicillin (100 μg/ml), with shaking at 220 rpm at 37° C.

vi) Plasmid DNA Preparation and Sequencing

Miniprep plasmid DNA was prepared from 5 ml cultures using a Qiaprep Turbo 9600 robotic system (Qiagen) or Wizard Plus SV Minipreps kit (Promega cat. no. 1460) according to the manufacturer's instructions. Plasmid DNA was eluted in 100 μl of sterile water. The DNA concentration was measured using an Eppendorf BO photometer. Plasmid DNA (200-500 ng) was subjected to DNA sequencing with T7 primer and SP6 primer using the BigDye Terminator system (Applied Biosystems cat. no. 4390246) according to the manufacturer's instructions. Sequencing reactions were purified using Dye-Ex columns (Qiagen) or Montage SEQ 96 cleanup plates (Millipore cat. no. LSKS09624) then analysed on an Applied Biosystems 3700 sequencer.

vii) Identification of cDNA Libraries Containing INSP002

PCR products obtained with INSP002-CP1 and INSP002-CP2 and migrating at the correct size (159 bp) were identified in the cortex, colon, fetal lung and fetal kidney cDNA libraries (libraries 8, 9, 11 and 12). The sequence of the PCR product cloned in pCRII-TOPO vector is shown in FIG. 7, and the plasmid map (plasmid ID 13422) is in FIG. 8.

The partial cDNA cloned is a portion of INSP002 exon 2, as shown by the alignment of the predicted INSP002 nucleotide sequence and the cloned partial nucleotide sequence in FIG. 9a and the alignment of the predicted INSP002 protein sequence and the cloned partial protein sequence in FIG. 9b.

Example 4

Generation of INSP002 ORF from Image: 4558384

Image clone 4558384 (in plasmid pOTB7) from retinoblastoma was purchased from Resgen (Invitrogen Corp). The *E. coli* stab of 4558384 was spread on an LB plate containing ampicillin (100 μg/ml) and grown up overnight at 37° C. Single ampicillin resistant colonies were inoculated into 5 ml LB containing ampicillin (100 μg/ml), and incubated with shaking at 220 rpm overnight at 37° C. Mini prep plasmid DNA was prepared and sequenced using SP6, T7, M13F, INSP002-CP1 and INSP002-CP2 primers as described in Example 3, vi).

The sequence of the insert is shown in FIG. 10. The alignment of the nucleotide and putative amino acid sequence of Image 4558384 cDNA with INSP002 is shown in FIG. 11. Image 4558384 cDNA appears to be a splice variant of INSP002. It contains an 87 bp insertion which introduces a frameshift and premature stop codon compared to the INSP002 predicted sequence. In addition the 3' untranslated sequence also contains an Alu repeat indicative of genomic DNA contamination of the cDNA. Exons 2 and 4 of Image 4558384 are equivalent to INSP002 prediction exons 1 and 2. However, Image 4558384 incorporates an extra exon between exons 1 and 2 of the INSP002 prediction. The extra exon encodes a premature stop codon which prevents translation of the cystine knot domain. The splice boundaries in Image 4558384 are as follows:

```
500       .    :    .    :    .    :    .    :    .    :
  492 GGCTGTGCCCTTCGTTCAG          ACACGGGAGTCTCGCTATGTTG
      ||||||||||||||||||>>>...>>>||||||||||||||||||||||
10234 GGCTGTGCCCTTCGTTCAGGTG...TAGACACGGGAGTCTCGCTATGTTG
      Exon2                         Exon3

550       .    :    .    :    .    :    .    :    .    :
  533 CCCAAGCTAGTCTTGAGCTTCTGGCCTCAAGCAATCCTCCCACCTCAGCC
      ||||||||||||||||||||||||||||||||||||||||||||||||||
10741 CCCAAGCTAGTCTTGAGCTTCTGGCCTCAAGCAATCCTCCCACCTCAGCC

600       .    :    .    :    .    :    .    :    .    :

583 TCC    GTTCTAG          GTGTTCTCCCGGCCCGGCTGCTCAGCCA
      |||  ||||||||>>>...>>>||||||||||||||||||||||||||
10791 TCC    GTTCTAGGTG...CAGGTGTTCTCCCGGCCCGGCTGCTCAGCCA
                                  Exon 4
```

A PCR strategy was devised to remove the genomic DNA in order to generate a full length cDNA encoding the INSP002 ORF. PCR primers were designed to amplify the 5' end (upstream) and 3' end (downstream) of the INSP002 sequence which flanked the 87 bp insertion in the Image clone. The reverse primer for the upstream sequence and the forward primer for the downstream sequence contained complementary sequences at their 3' and 5' ends respectively to provide overlapping ends, so that the PCR products from each reaction could be mixed and annealed together, allowing amplification of the full length cDNA in a third PCR reaction, using a nested upstream forward primer and a nested reverse downstream primer.

The first PCR reaction to amplify the 5' end of INSP002 (upstream of the 87 bp insertion) contained, in a final volume of 50 µl: 5 µl 10× Platinum Pfx buffer, 1.5 µl dNTPs (10 mM), 1 µl MgSO4 (50 mM), 1.5 µl of INSP002V-5'-F (10 µM), 1.5 µl INSP002V-5'-R (10 µM), 0.75 µl Platinum Pfx and 135 ng IMAGE:4558384 plasmid cDNA. The amplification conditions were 1 cycle of 94° C. for 2 min, 30 cycles of 94° C., 15 s and 68° C., 1 min; and 1 cycle of 68° C. for 7 min. The second PCR reaction to amplify the 3' end of INSP002 (downstream of the 87 bp insertion) was performed under the same conditions except that the primers were: INSP002V-3'-F and INSP002V-3'-R.

The amplification products were visualized on 0.8% agarose gels in 1× TAE buffer (Invitrogen). PCR products migrating at the predicted molecular mass (520 bp and 448 bp, for PCR 1 and 2 respectively) were purified from the gel using the Wizard PCR Preps DNA Purification System (Promega). PCR products were eluted in 50 µl of sterile water and the DNA concentration was measured using an Eppendorf BO photometer. Fifty ng of each purified PCR product was then used as a template for a nested PCR in a 50 µl reaction containing 5 µl 10× Platinum Pfx buffer, 1.5 µl dNTPs (10 mM), 1 µl MgSO4 (50 mM), 1.5 µl of INSP002V-5'nest-F (10 µM) and 1.5 µl INSP002V-3'nest-R (10 µM). The reaction mix was heated at 95° C. for 3 min and 0.75 µl Platinum Pfx polymerase added. The amplification conditions were as follows: 1 cycle of 94° C. for 2 min; 30 cycles of 94° C., 15 s; 61° C., 30 s and 68° C., 1 min; and 1 cycle of 68° C. for 7 min. PCR products migrating at the predicted molecular mass of 719 bp were purified from the gel using the Wizard PCR Preps DNA Purification System and eluted in 50 µl sterile water. Four µl of the purified PCR product was then ligated into pCR4 blunt TOPO vector as described in section 1.4. Ampicillin resistant colonies were tested for inserts by colony PCR using T3 and T7 primers as described in section 1.5. Colonies which gave the expected PCR product size (719 bp+106 bp due to the multiple cloning site or MCS) were grown up in 5 ml LB containing ampicillin (100 µg/ml), overnight with shaking at 220 rpm, at 37° C. Miniprep plasmid DNA was prepared from 5 ml cultures and sequenced with T3 and T7 primers as described in section 1.6. The sequence of one of the resulting clones and the corresponding plasmid map (pCR4 blunt TOPO-INSP002V) are shown in FIGS. 12 and 13 respectively. Translation of the cloned sequence indicates that INSP002V contains a 2 amino acid deletion (ΔV107 and ΔQ108) and a single amino acid substitution (F110L) compared to the predicted INSP002 sequence. Alignment of the nucleotide and amino acid sequences for the INSP002 prediction and INSP002V are shown in FIG. 14.

When compared to the INSP002 prediction, the splice junction between exons 1 and 2 uses a 6 bp upstream donor site. This results in the deletion of two amino acids (ValGlu). The splice acceptor used is the same as that used by the INSP002 prediction, however there are two sequencing errors after the acceptor. This results in an amino acid substitution (Phe->Leu).

Example 5

Construction of a Plasmid for the Expression of INSP002V in HEK293/EBNA Cells

A pCR4 blunt-TOPO clone containing the full coding sequence (ORF) of INSP002V identified by DNA sequencing (FIG. 13) was then used to subclone the insert into the mammalian cell expression vector pEAK12d (FIG. 15) using the Gateway™ cloning methodology (Invitrogen).

i) Generation of Gateway Compatible INSP002 ORF Fused to an in Frame 6HIS Tag Sequence.

The first stage of the Gateway cloning process involves a two step PCR reaction which generates the ORF of INSP002V flanked at the 5' end by an attB1 recombination site and Kozak sequence, and flanked at the 3' end by a sequence encoding an in-frame 6 histidine (6HIS) tag, a stop codon and the attB2 recombination site (Gateway compatible cDNA). The first PCR reaction (in a final volume of 50 µl) contains: 25 ng of pCR4 blunt TOPO-INSP002V (plasmid 13075 and FIG. 13), 1.5 µl dNTPs (10 mM), 5 µl of 10× Pfx polymerase buffer, 1 µl MgSO4 (50 mM), 0.5 µl each of gene specific primer (100 µM) (INSP002V-EX1 and INSP002V EX2) and 0.5 µl Platinum Pfx DNA polymerase (Invitrogen). The PCR reaction was performed using an initial denaturing step of 95° C. for 2 min, followed by 12 cycles of 94° C., 15 sec and 68° C. for 30 sec. PCR products were purified directly from the reaction mixture using the Wizard PCR prep DNA purification system (Promega) according to the manufacturer's instructions. The second PCR reaction (in a final volume of 50 µl) contained 10 µl purified PCR product, 1.5 µl dNTPs (10 mM), 1 µl MgSO4 (50 mM), 5 µl of 10× Platinum Pfx polymerase buffer, 0.5 µl of each Gateway conversion primer (100 µM) (GCP forward and GCP reverse) and 0.5 µl of Platinum Pfx DNA polymerase. The conditions for the 2nd PCR reaction were: 95° C. for 1 min; 4 cycles of 94° C., 15 sec; 45° C., 30 sec and 68° C. for 3.5 min; 25 cycles of 94° C., 15 sec; 55° C., 30 sec and 68° C., 3.5 min. PCR products were purified as described above.

ii) Subcloning of Gateway Compatible INSP002V ORF into Gateway Entry Vector pDONR201 and Expression Vector pEAK12d The second stage of the Gateway cloning process involves subcloning of the Gateway modified PCR product into the Gateway entry vector pDONR201 (Invitrogen, FIG. 16) as follows: 5 µl of purified PCR product is incubated with 1.5 µl pDONR201 vector (0.1 µg/µl), 2 µl BP buffer and 1.5 µl of BP clonase enzyme mix (Invitrogen) at RT for 1 h. The reaction was stopped by addition of proteinase K (2 µg) and incubated at 37° C. for a further 10 min. An aliquot of this reaction (2 µl) was transformed into E. coli DH10B cells by electroporation using a Biorad Gene Pulser. Transformants were plated on LB-kanamycin plates. Plasmid mini-prep DNA was prepared from 1-4 of the resultant colonies using Wizard Plus SV Minipreps kit (Promega), and 1.5 µl of the plasmid eluate was then used in a recombination reaction containing 1.5 µl pEAK12d vector (FIG. 9) (0.1 µg/µl), 2 µl LR buffer and 1.5 µl of LR clonase (Invitrogen) in a final volume of 10 µl. The mixture was incubated at RT for 1 h, stopped by addition of proteinase K (2 µg) and incubated at 37° C. for a further 10 min. An aliquot of this reaction (1 µl) was used to transform E. coli DH10B cells by electroporation.

Clones containing the correct insert were identified by performing colony PCR as described above except that pEAK12d primers (pEAK12d F and pEAK12d R) were used for the PCR. Plasmid mini prep DNA was isolated from clones containing the correct insert using a Qiaprep Turbo 9600 robotic system (Qiagen) or manually using a Wizard Plus SV minipreps kit (Promega) and sequence verified using the pEAK12d F and pEAK12d R primers.

CsCl gradient purified maxi-prep DNA of plasmid pEAK12d-INSP002V-6HIS (plasmid ID number 13227, FIG. 17) was prepared from a 500 ml culture of sequence verified clones (Sambrook J. et al., in Molecular Cloning, A Laboratory Manual, $2^{nd}$ edition, 1989, Cold Spring Harbor Laboratory Press), resuspended at a concentration of 1 □g/□l in sterile water and stored at −20 C.

iii) Construction of Expression Vector pEAK12d

The vector pEAK12d is a Gateway Cloning System compatible version of the mammalian cell expression vector pEAK12 (purchased from Edge Biosystems) in which the cDNA of interest is expressed under the control of the human EF1α promoter. pEAK12d was generated as described below:

pEAK12 was digested with restriction enzymes HindIII and NotI, made blunt ended with Klenow (New England Biolabs) and dephosphorylated using calf-intestinal alkaline phosphatase (Roche). After dephosphorylation, the vector was ligated to the blunt ended Gateway reading frame cassette C (Gateway vector conversion system, Invitrogen cat no. 11828-019) which contains AttR recombination sites flanking the ccdB gene and chloramphenicol resistance, and transformed into *E. coli* DB3.1 cells (which allow propagation of vectors containing the ccdB gene). Mini prep DNA was isolated from several of the resultant colonies using a Wizard Plus SV Minipreps kit (Promega) and digested with AseI/EcoRI to identify clones yielding a 670 bp fragment, indicating that the cassette had been inserted in the correct orientation. The resultant plasmid was called pEAK12d (FIG. 15).

Example 6

Expression in Mammalian Cells and Purification of the INSP002-SV-6His-V1 (Plasmid #13227)

Human Embryonic Kidney 293 cells expressing the Epstein-Barr virus Nuclear Antigen (HEK293-EBNA, Invitrogen) were maintained in suspension in Ex-cell VPRO serum-free medium (seed stock, maintenance medium, JRH). Sixteen to 20 hours prior to transfection (Day-1), cells were seeded in 2× T225 flasks (50 ml per flask in DMEM/F12 (1:1) containing 2% FBS seeding medium (JRH) at a density of 2× $10^5$ cells/ml). The next day (transfection day 0) the transfection took place by using the JetPEI™ reagent (2 µl/µg of plasmid DNA, PolyPlus-transfection). For each flask, 113 µg of cDNA (number #13227) was co-transfected with 2.3 µg of GFP (fluorescent reporter gene). The transfection mix was then added to the 2× T225 flasks and incubated at 37° C. (5% $CO_2$) for 6 days. In order to increase our chances to get more material, we repeated this procedure into two extra flasks such as to generate 200 ml total. Confirmation of positive transfection was done by qualitative fluorescence examination at day 1 and day 6 (Axiovert 10 Zeiss).

On day 6 (harvest day), supernatants (200 ml) from the four flasks were pooled and centrifuged (4° C., 400 g) and placed into a pot bearing a unique identifier.

One aliquot (500 ul) was kept for QC of the 6His-tagged protein (internal bioprocessing QC).

Purification Process

The 200 ml culture medium sample containing the recombinant protein with a C-terminal 6His tag was diluted to a final volume of 400 ml with cold buffer A (50 mM $NaH_2PO_4$; 600 mM NaCl; 8.7% (w/v) glycerol, pH 7.5). The sample was filtered through a 0.22 µm sterile filter (Millipore, 500 ml filter unit) and kept at 4° C. in a 500 ml sterile square media bottle (Nalgene).

The purification was performed at 4° C. on the VISION workstation (Applied Biosystems) connected to an automatic sample loader (Labomatic). The purification procedure was composed of two sequential steps, metal affinity chromatography on a Poros 20 MC (Applied Biosystems) column charged with Ni ions (4.6× 50 mm, 0.83 ml), followed by gel filtration on a Sephadex G-25 medium (Amersham Pharmacia) column (1,0×10 cm).

For the first chromatography step the metal affinity column was regenerated with 30 column volumes of EDTA solution (100 mM EDTA; 1 M NaCl; pH 8.0), recharged with Ni ions through washing with 15 column volumes of a 100 mM $NiSO_4$ solution, washed with 10 column volumes of buffer A, followed by 7 column volumes of buffer B (50 mM $NaH_2PO_4$; 600 mM NaCl; 8.7% (w/v) glycerol, 400 mM; imidazole, pH 7.5), and finally equilibrated with 15 column volumes of buffer A containing 15 mM imidazole. The sample was charged onto the Ni metal affinity column in batches of 200 ml. The Labomatic sample loader transferred 200 ml of the sample into a 200 ml sample loop and this sample was subsequently charged onto the Ni metal affinity column at a flow rate of 10 ml/min. The transfer and charging procedure was repeated once to load the 400 ml sample onto the column. At the end of the charging procedure the column was washed with 12 column volumes of buffer A, followed by 28 column volumes of buffer A containing 20 mM imidazole. During the 20 mM imidazole wash loosely attached contaminating proteins were elution of the column. The recombinant His-tagged protein was finally eluted with 10 column volumes of buffer B at a flow rate of 2 ml/min, and the eluted protein was collected in a 1.6 ml fraction.

For the second chromatography step, the Sephadex G-25 gel-filtration column was regenerated with 2 ml of buffer D (1.137 M NaCl; 2.7 mM KCl; 1.5 mM $KH_2PO_4$; 8 mM $Na_2HPO_4$; pH 7.2), and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the Ni-column was automatically, through the integrated sample loader on the VISION, loaded onto the Sephadex G-25 column and the protein was eluted with buffer C at a flow rate of 2 ml/min. The desalted sample was recovered in a 2.2 ml fraction. The fraction was filtered through a 0.22 µm sterile centrifugation filter (Millipore), aliquoted, frozen and stored at −80C. An aliquot of the sample was analyzed on SDS-PAGE (4-12% NuPAGE gel; Novex) Western blot with anti-His antibodies.

Following the electrophoresis the proteins were electrotransferred from the gel to a nitrocellulose membrane at 290 mA for 1 hour at 4° C. The membrane was blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 h at room temperature, and subsequently incubated with a mixture of 2 rabbit polyclonal anti-His antibodies (G-18 and H-15, 0.2 ug/ml each; Santa Cruz) in 2.5% milk powder in buffer E overnight at 4° C. After further 1 hour incubation at room temperature, the membrane was washed with buffer E (3× 10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3× 10 minutes), the membrane was developed with the ECL kit (Amersham Pharmacia) for 1 min. The membrane was subsequently exposed to a Hyperfilm (Amersham Pharmacia), the film developed and the western blot image visually analyzed.

Example 7

Cloning of Full Length INSP002 from Heart

The full length coding sequence of INSP002 was cloned from heart cDNA as follows:

i) Generation of Heart cDNA Template

Human heart total RNA from was purchased from Clontech. The quality and concentration of the RNA was analysed using an Agilent 2100 Bioanalyzer.

For cDNA synthesis the reaction mixture contained: 1 µl oligo (dT)$_{15}$ primer (500 µg/ml, Promega cat. no. C 1101), 2 µg total RNA, 1 µl dNTPs (10 mM) in a volume of 12 µl. The mixture was heated to 65° C. for 5 min and then chilled on ice. The following reagents were then added: 4 µl 5× first strand buffer, 2 µl DTT (0.1 M), 1 µl RNAseOut recombinant ribonuclease inhibitor (40 units/µl, Promega, cat. no. N 2511) and incubated at 42° C. for 2 min before addition of 1 µl (200 units) of Superscript II (Invitrogen cat. no. 18064-014). The mixture was incubated at 42° C. for 50 min and then heated at 70° C. for 15 min. To remove the RNA template, 1 µl (2 units) of *E. coli* RNase H (Invitrogen cat. no. 18021-014) was added and the reaction mixture further incubated at 37° C. for 20 min. The final reaction mix was diluted to 200 µl with sterile water and stored at −80 C.

ii) Cloning of the Full Length Coding Sequence of INSP002 by PCR

The full length coding sequence of INSP002 was cloned from human heart cDNA by PCR in a 50 µl PCR reaction mixture containing 5 µl heart cDNA, 5 µl 10× Pfx buffer, 1.5 µl dNTPs (10 mM), 1 µL MgSO4 (50 mM), 1.5 µl gene specific forward primer INSP002-FL-F (10 µM), 1.5 µl gene specific reverse primer INSP002-FL-R (10 µM) and 0.5 µl Platinum Pfx DNA polymerase (Invitrogen). The cycling conditions were 1 cycle of 94° C., 4 min; 35 cycles of 94° C., 15 sec; 55° C., 30 s; 68° C., 1 min; 1 cycle of 68° C., 10 min followed by a holding cycle at 4° C.

The amplification products were visualized on 0.8% agarose gels in 1× TAE buffer (Invitrogen) and PCR products migrating at the predicted molecular mass (589 bp) were purified from the gel using the Qiagen MinElute Gel Extraction kit (Qiagen). PCR products were eluted in 50 µl of 10 mM Tris-HCl pH 8.5 and subcloned into pCR4 blunt TOPO vector as described previously (section 1.4) Several ampicilin resistant colonies were subjected to colony PCR as described in section 1.5. Colonies containing the correct size insert (589 bp++106 bp due to the MCS) were grown up overnight at 37° C. in 5 ml L-Broth (LB) containing ampicillin (100 µg/ml), with shaking at 220 rpm at 37° C. Miniprep plasmid DNA was prepared from 5 ml cultures using a Qiaprep Turbo 9600 robotic system (Qiagen) or Wizard Plus SV Minipreps kit (Promega cat. no. 1460) according to the manufacturer's instructions and 200-500 ng of mini-prep DNA was sequenced as described in section 1.6 with T3 and T7 primers (Table III). The cloned sequence is given in FIG. 18. The map of the resultant plasmid, pCR4-blunt TOPO-INSP002FL (plasmid ID. No. 13514) is shown in FIG. 19.

TABLE I

Human cDNA libraries

| Library | Tissue/cell source | Vector | Host strain | Supplier | Cat. no. |
|---|---|---|---|---|---|
| 1 | Human fetal brain | Zap II | XL1-Blue MRF' | Stratagene | 936206 |
| 2 | Human ovary | GT10 | LE392 | Clontech | HL1098a |
| 3 | Human pituitary | GT10 | LE392 | Clontech | HL1097a |
| 4 | Human placenta | GT11 | LE392 | Clontech | HL1075b |
| 5 | Human testis | GT11 | LE392 | Clontech | HL1010b |
| 6 | Human sustanta nigra | GT10 | LE392 | in house | |
| 7 | Human fetal brain | GT10 | LE392 | in house | |
| 8 | Human cortex brain | GT10 | LE392 | in house | |
| 9 | Human colon | GT10 | LE392 | Clontech | HL1034a |
| 10 | Human fetal brain | GT10 | LE392 | Clontech | HL1065a |
| 11 | Human fetal lung | GT10 | LE392 | Clontech | HL1072a |
| 12 | Human fetal kidney | GT10 | LE392 | Clontech | HL1071a |
| 13 | Human fetal liver | GT10 | LE392 | Clontech | HL1064a |
| 14 | Human bone marrow | GT10 | LE392 | Clontech | HL1058a |
| 15 | Human peripheral blood monocytes | GT10 | LE392 | Clontech | HL1050a |
| 16 | Human placenta | GT10 | LE392 | in house | |
| 17 | Human SHSYSY | GT10 | LE392 | in house | |
| 18 | Human U373 cell line | GT10 | LE392 | in house | |
| 19 | Human CFPoc-1 cell line | Uni Zap | XL1-Blue MRF' | Stratagene | 936206 |
| 20 | Human retina | GT10 | LE392 | Clontech | HL1132a |
| 21 | Human urinary bladder | GT10 | LE392 | in house | |
| 22 | Human platelets | Uni Zap | XL1-Blue MRF' | in house | |
| 23 | Human neuroblastoma Kan + TS | GT10 | LE392 | in house | |
| 24 | Human bronchial smooth muscle | GT10 | LE392 | in house | |
| 25 | Human bronchial smooth muscle | GT10 | LE392 | in house | |
| 26 | Human Thymus | GT10 | LE392 | Clontech | HL1127a |
| 27 | Human spleen 5' stretch | GT11 | LE392 | Clontech | HL1134b |
| 28 | Human peripherical blood monocytes | GT10 | LE392 | Clontech | HL1050a |
| 29 | Human testis | GT10 | LE392 | Clontech | HL1065a |
| 30 | Human fetal brain | GT10 | LE392 | Clontech | HL1065a |

TABLE I-continued

Human cDNA libraries

| Library | Tissue/cell source | Vector | Host strain | Supplier | Cat. no. |
|---|---|---|---|---|---|
| 31 | Human substancia Nigra | GT10 | LE392 | Clontech | HL1093a |
| 32 | Human placenta #11 | GT11 | LE392 | Clontech | HL1075b |
| 33 | Human Fetal brain | GT10 | LE392 | Clontech | custom |
| 34 | Human placenta #59 | GT10 | LE392 | Clontech | HL5014a |
| 35 | Human pituirary | GT10 | LE392 | Clontech | HL1097a |
| 36 | Human pancreas #63 | Uni Zap XR | XL1-Blue MRF' | Stratagene | 937208 |
| 37 | Human placenta #19 | GT11 | LE392 | Clontech | HL1008 |
| 38 | Human liver 5'strech | GT11 | LE392 | Clontech | HL1115b |
| 39 | Human uterus | Zap-CMV XR | XL1-Blue MRF' | Stratagene | 980207 |
| 40 | Human kidney large-insert cDNA library | TriplEx2 | XL1-Blue | Clontech | HL5507u |

TABLE II

INSP002 Cloning primers

| Primer | Sequence (5'-3') |
|---|---|
| INSP002-CP1 | CTC AGC CAT ACG CCT CCG AA |
| INSP002-CP2 | GCT GAG CTG CCA GTG AGA CA |
| INSP002V-5'-F | ACC TGG AAG GAA GCG ACT GCA CTG A |
| INSP002V-5'-R | GCA GCC GGG CCG GGA GAG AAC GAA GGG CAC AGC CTT A |
| INSP002V-3'-F | AGG CTG TGC CCT TCG TTC TCT CCC GGC CCG GCT GCT C |
| INSP002V-3'-R | ACT CCA GGA CGG GCA CTG TGT CTA C |
| INSP002V-5'nest-F | GTC GAC TGC TAG TGA CCT TGA G |
| INSP002V-3'nest-R | ACA TCA TCC AGG TCC ACG TCT T |

TABLE III

Primers for INSP002 subcloning and sequencing

| Primer | Sequence (5'-3') |
|---|---|
| SP6 | ATT TAG GTG ACA CTA TAG |
| T7 | TAA TAC GAC TCA CTA TAG GG |
| T3 | ATT AAC CCT CAC TAA AGG GA |
| M13F | TGT AAA ACG ACG GCC AGT |
| pEAK12-F | GCC AGC TTG GCA CTT GAT GT |
| pEAK12-R | GAT GGA GGT GGA CGT GTC AG |
| INSP002V-EX1 | AA GCA GGC TTC GCC ACC ATG CTC CTT GGC CAG CTA TC |
| INSP002V-EX2 | GTG ATG GTG ATG GTG TGC TTT TGG GCT GCA GTG AC |
| GCP Forward | G GGG ACA AGT TTG TAC AAA AAA GCA GGC TTC GCC ACC |
| GCP Reverse | GGG GAC CAC TTT GTA CAA GAA AGC TGG GTT TCA ATG GTG ATG GTG ATG GTG |

TABLE IV

PCR primers for cloning of full length INSP002

| Primer | Sequence (5'-3') |
|---|---|
| INSP002-FL-F | GAT GCT CCT TGG CCA GCT AT |
| INSP002-FL-R | CCA TCC ACG ATG CTC AGT TC |

Underlined sequence = Kozak sequence
Bold = Stop codon
*Italic* sequence = His tag The invention will now be further described by the following numbered paragraphs:

1. A polypeptide, which polypeptide:
   (i) comprises the amino acid sequence as recited in SEQ ID NO:6 or SEQ ID NO:8,
   (ii) is a fragment thereof having the function of a secreted protein, preferably the function of a member of the cystine knot fold cytokine superfamily, preferably the function of a member of the DAN subfamily, or having an antigenic determinant in common with the polypeptide of (i); or
   (iii) is a functional equivalent of (i) or (ii).

2. A polypeptide according to paragraph 1 which:
   (i) consists of the amino acid sequence as recited in, SEQ ID NO:6 or SEQ ID NO:8,
   (ii) is a fragment thereof having the function of a secreted protein, preferably the function of a member of the cystine knot fold cytokine superfamily, preferably the function of a member of the DAN subfamily, or having an antigenic determinant in common with the polypeptide of (i); or
   (iii) is a functional equivalent of (i) or (ii).

3. A polypeptide which is a functional equivalent according to part (iii) of paragraph 1 or paragraph 2, characterised in that it is homologous to the amino acid sequence as recited in SEQ ID NO:6 or SEQ ID NO:8 and has cystine knot fold cytokine activity, preferably the activity of a member of DAN subfamily.

4. A polypeptide which is a fragment or a functional equivalent as recited to any one of paragraphs 1 to 3, which has greater than 35% sequence identity with the amino acid sequence recited in SEQ ID NO:6 or SEQ ID NO:8, or with an active fragment thereof, preferably greater than 40%, 50%, 60%, 70%, 80%, 90%, 95%, 98% or 99% sequence identity.

5. A polypeptide which is a functional equivalent as recited in any one of paragraphs 1 to 4, which exhibits significant structural homology with a polypeptide having the amino acid sequence recited in SEQ ID NO:6 or SEQ ID NO:8.
6. A polypeptide which is a fragment as recited in any one of paragraph 1, 2 or 4 having an antigenic determinant in common with the polypeptide of part (i) of any one of paragraphs 1 to 3 which consists of 7 or more amino acid residues from the amino acid sequence recited in SEQ ID NO:6 or SEQ ID NO:8.
7. A purified nucleic acid molecule which encodes a polypeptide according to any one of the preceding paragraphs.
8. A purified nucleic acid molecule according to paragraph 7, which comprises the nucleic acid sequence as recited in SEQ ID NO:5, or is a redundant equivalent or fragment thereof.
9. A purified nucleic acid molecule according to paragraph 7 which consists of the nucleic acid sequence as recited in SEQ ID NO:5, or is a redundant equivalent or fragment thereof.
10. A purified nucleic acid molecule according to paragraph 7 which comprises nucleotides 152 to 721 of the nucleic acid sequence recited in SEQ ID NO:5 (SEQ ID NO:11).
11. A purified nucleic acid molecule according to paragraph 7 which consists of nucleotides 152 to 721 of the nucleic acid sequence recited in SEQ ID NO:5 (SEQ ID NO:11).
12. A purified nucleic acid molecule according to paragraph 7 which comprises nucleotides 218 to 721 of the nucleic acid sequence recited in SEQ ID NO:5 (SEQ ID NO:9).
13. A purified nucleic acid molecule according to paragraph 7 which consists of nucleotides 218 to 721 of the nucleic acid sequence recited in SEQ ID NO:5 (SEQ ID NO:9).
14. A purified nucleic acid molecule which hydridizes under high stringency conditions with a nucleic acid molecule according to any one of paragraphs 8 to 13.
15. A vector comprising a nucleic acid molecule as recited in any one of paragraphs 8 to 14.
16. A host cell transformed with a vector according to paragraph 15.
17. A ligand which binds specifically to, and which preferably inhibits the cystine knot fold cytokine activity, preferably the DAN subfamily activity of a polypeptide according to any one of paragraphs 1 to 6.
18. A ligand according to paragraph 17, which is an antibody.
19. A compound that either increases or decreases the level of expression or activity of a polypeptide according to any one of paragraphs 1 to 6.
20. A compound according to paragraph 19 that binds to a polypeptide according to any one of paragraphs 1 to 6 without inducing any of the biological effects of the polypeptide.
21. A compound according to paragraph 20, which is a natural or modified substrate, ligand, enzyme, receptor or structural or functional mimetic.
22. A polypeptide according to any one of paragraphs 1 to 6, a nucleic acid molecule according to any one of paragraphs 7 to 14, a vector according to paragraph 15, a ligand according to paragraph 16 or paragraph 17, or a compound according to any one of paragraphs 19 to 21, for use in therapy or diagnosis of disease.
23. A method of diagnosing a disease in a patient, comprising assessing the level of expression of a natural gene encoding a polypeptide according to any one of paragraphs 1 to 6, or assessing the activity of a polypeptide according to any one of paragraphs 1 to 6, in tissue from said patient and comparing said level of expression or activity to a control level, wherein a level that is different to said control level is indicative of disease.
24. A method according to paragraph 23 that is carried out in vitro.
25. A method according to paragraph 23 or paragraph 24, which comprises the steps of: (a) contacting a ligand according to paragraph 17 or paragraph 18 with a biological sample under conditions suitable for the formation of a ligand-polypeptide complex; and (b) detecting said complex.
26. A method according to paragraph 23 or paragraph 24, comprising the steps of:
    a) contacting a sample of tissue from the patient with a nucleic acid probe under stringent conditions that allow the formation of a hybrid complex between a nucleic acid molecule according to any one of paragraphs 7 to 14 and the probe;
    b) contacting a control sample with said probe under the same conditions used in step a); and
    c) detecting the presence of hybrid complexes in said samples; wherein detection of levels of the hybrid complex in the patient sample that differ from levels of the hybrid complex in the control sample is indicative of disease.
27. A method according to paragraph 23 or paragraph 24, comprising:
    a) contacting a sample of nucleic acid from tissue of the patient with a nucleic acid primer under stringent conditions that allow the formation of a hybrid complex between a nucleic acid molecule according to any one of paragraphs 7 to 14 and the primer;
    b) contacting a control sample with said primer under the same conditions used in step a); and
    c) amplifying the sampled nucleic acid; and
    d) detecting the level of amplified nucleic acid from both patient and control samples; wherein detection of levels of the amplified nucleic acid in the patient sample that differ significantly from levels of the amplified nucleic acid in the control sample is indicative of disease.
28. A method according to paragraph 23 or paragraph 24 comprising:
    a) obtaining a tissue sample from a patient being tested for disease;
    b) isolating a nucleic acid molecule according to any one of paragraphs 7 to 14 from said tissue sample; and
    c) diagnosing the patient for disease by detecting the presence of a mutation which is associated with disease in the nucleic acid molecule as an indication of the disease.
29. The method of paragraph 28, further comprising amplifying the nucleic acid molecule to form an amplified product and detecting the presence or absence of a mutation in the amplified product.
30. The method of paragraph 28 or paragraph 29, wherein the presence or absence of the mutation in the patient is detected by contacting said nucleic acid molecule with a nucleic acid probe that hybridises to said nucleic acid molecule under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation.
31. A method according to any one of paragraphs 23 to 30, wherein said disease is a cell proliferative disorder, autoimmune/inflammatory disorder, cardiovascular disorder, neurological disorder, developmental disorder, metabolic disorder, infection or other pathological condition.

32. Use of a polypeptide according to any one of paragraphs 1 to 6 as a secreted protein.
33. Use of a polypeptide according to any one of paragraphs 1 to 6 as a cytokine, preferably a cystine knot fold cytokine, preferably as a member of the DAN subfamily of cystine knot fold cytokines.
34. A pharmaceutical composition comprising a polypeptide according to any one of paragraphs 1 to 6, a nucleic acid molecule according to any one of paragraphs 7 to 14, a vector according to paragraph 15, a ligand according to paragraph 17 or paragraph 18, or a compound according to any one of paragraphs 19 to 21.
35. A vaccine composition comprising a polypeptide according to any one of paragraphs 1 to or a nucleic acid molecule according to any one of paragraphs 7 to 14.
36. A polypeptide according to any one of paragraphs 1 to 6, a nucleic acid molecule according to any one of paragraphs 7 to 14, a vector according to paragraph 15, a ligand according to paragraph 17 or paragraph 18, a compound according to any one of paragraphs 19 to 21, or a pharmaceutical composition according to paragraph 34, for use in the manufacture of a medicament for the treatment of cell proliferative disorders, autoimmune/inflammatory disorders, cardiovascular disorders, neurological disorders, developmental disorders, metabolic disorders, infections and other pathological conditions.
37. A method of treating a disease in a patient, comprising administering to the patient a polypeptide according to any one of paragraphs 1 to 6, a nucleic acid molecule according to any one of paragraphs 7 to 14, a vector according to paragraph 15, a ligand according to paragraph 17 or paragraph 18, a compound according to any one of paragraphs 19 to 21, or a pharmaceutical composition according to paragraph 34.
38. A method according to paragraph 37, wherein, for diseases in which the expression of the natural gene or the activity of the polypeptide is lower in a diseased patient when compared to the level of expression or activity in a healthy patient, the polypeptide, nucleic acid molecule, vector, ligand, compound or composition administered to the patient is an agonist.
39. A method according to paragraph 37, wherein, for diseases in which the expression of the natural gene or activity of the polypeptide is higher in a diseased patient when compared to the level of expression or activity in a healthy patient, the polypeptide, nucleic acid molecule, vector, ligand, compound or composition administered to the patient is an antagonist.
40. A method of monitoring the therapeutic treatment of disease in a patient, comprising monitoring over a period of time the level of expression or activity of a polypeptide according to any one of paragraphs 1 to 6, or the level of expression of a nucleic acid molecule according to any one of paragraphs 7 to 14 in tissue from said patient, wherein altering said level of expression or activity over the period of time towards a control level is indicative of regression of said disease.
41. A method for the identification of a compound that is effective in the treatment and/or diagnosis of disease, comprising contacting a polypeptide according to any one of paragraphs 1 to 6, or a nucleic acid molecule according to any one of paragraphs 7 to 14 with one or more compounds suspected of possessing binding affinity for said polypeptide or nucleic acid molecule, and selecting a compound that binds specifically to said nucleic acid molecule or polypeptide.
42. A kit useful for diagnosing disease comprising a first container containing a nucleic acid probe that hybridises under stringent conditions with a nucleic acid molecule according to any one of paragraphs 7 to 14; a second container containing primers useful for amplifying said nucleic acid molecule; and instructions for using the probe and primers for facilitating the diagnosis of disease.
43. The kit of paragraph 42, further comprising a third container holding an agent for digesting unhybridised RNA.
44. A kit comprising an array of nucleic acid molecules, at least one of which is a nucleic acid molecule according to any one of paragraphs 7 to 14.
45. A kit comprising one or more antibodies that bind to a polypeptide as recited in any one of paragraphs 1 to 6; and a reagent useful for the detection of a binding reaction between said antibody and said polypeptide.
46. A transgenic or knockout non-human animal that has been transformed to express higher, lower or absent levels of a polypeptide according to any one of paragraphs 1 to 6.
47. A method for screening for a compound effective to treat disease, by contacting a non-human transgenic animal according to paragraph 46 with a candidate compound and determining the effect of the compound on the disease of the animal.

The invention claimed is:

1. An isolated polypeptide that consists of the amino acid sequence as recited in SEQ ID NO: 2, SEQ ID NO:4, SEQ ID NO:6, SEQ ID NO: 7, SEQ ID NO:8, or SEQ ID NO: 14.

2. A composition comprising a polypeptide according to claim 1 and a pharmaceutically acceptable carrier.

3. An isolated polypeptide that consists of the amino acid sequence of SEQ ID NO: 14.

* * * * *

UNITED STATES PATENT AND TRADEMARK OFFICE
CERTIFICATE OF CORRECTION

PATENT NO. : 7,619,065 B2  
APPLICATION NO. : 10/872898  
DATED : November 17, 2009  
INVENTOR(S) : Davies et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 400 days.

Signed and Sealed this

Twenty-sixth Day of October, 2010

David J. Kappos  
*Director of the United States Patent and Trademark Office*